United States Patent
Saito et al.

(10) Patent No.: US 10,889,853 B2
(45) Date of Patent: Jan. 12, 2021

(54) RNA MICROARRAY FOR DETECTING INTERACTION BETWEEN PROTEIN AND RNA CONTAINING A HIGHER-ORDER STRUCTURE

(71) Applicant: KYOTO UNIVERSITY, Kyoto (JP)

(72) Inventors: Hirohide Saito, Kyoto (JP); Toshiki Taya, Kyoto (JP); Shunichi Kashida, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/562,470

(22) Filed: Sep. 6, 2019

(65) Prior Publication Data

US 2020/0048685 A1  Feb. 13, 2020

Related U.S. Application Data

(62) Division of application No. 15/110,516, filed as application No. PCT/JP2015/050494 on Jan. 9, 2015, now Pat. No. 10,435,738.

(30) Foreign Application Priority Data

Jan. 10, 2014 (JP) .................................. 2014-003734

(51) Int. Cl.
C12Q 1/6816 (2018.01)
C12Q 1/6806 (2018.01)
C12Q 1/6811 (2018.01)
C12Q 1/6818 (2018.01)
C12Q 1/6834 (2018.01)

(52) U.S. Cl.
CPC ......... *C12Q 1/6816* (2013.01); *C12Q 1/6806* (2013.01); *C12Q 1/6811* (2013.01); *C12Q 1/6818* (2013.01); *C12Q 1/6834* (2013.01)

(58) Field of Classification Search
CPC .. C12Q 1/6816; C12Q 1/6806; C12Q 1/6811; C12Q 1/6818; C12Q 1/6834
See application file for complete search history.

(56) References Cited

U.S. PATENT DOCUMENTS

| 2005/0059049 A1 | 3/2005 | Moen et al. |
| 2006/0199183 A1 | 9/2006 | Valat et al. |
| 2011/0230367 A1 | 9/2011 | Yu et al. |

FOREIGN PATENT DOCUMENTS

| JP | 2002181813 | 6/2002 |
| JP | 2006520206 | 9/2006 |
| JP | 2007529994 | 11/2007 |
| JP | 2009142273 | 7/2009 |
| WO | 2009/066758 | 5/2009 |
| WO | 2010/067811 | 6/2010 |

OTHER PUBLICATIONS

Hentze et al. ("A brave new world of RNA-binding proteins", Nature Reviews Molecular Cell Biology vol. 19, pp. 327-341(2018)).*
Japanese Office Action corresponding to Japanese Patent Application No. 2015-556845, dated Nov. 16, 2018, 10 pages, English translation.
Keene, Jack D. "RNA regulons: coordination of post-transcriptional events" Nature Reviews Genetics 8:533-543 (2007).
M. A. Newman et al: "Deep sequencing of microRNA precursors reveals extensive 3' end modification", RNA vol. 17, No. 10, Aug. 17, 2011 (Aug. 17, 2011), pp. 1795-1803. XP055391698.
Nam et al. "Molecular Basis for Interaction of let-7 MicroRNAs with Lin28" Cell 147:1080-1091 (2011).
Ray et al. "A compendium of RNA-binding motifs for decoding gene regulation" Nature 499:172-177 (2013).
Silva et al. "Second-generation shRNA libraries covering the mouse and human genomes", Nature Genetics, Nature Publishing Group, New York, US, vol. 37, No. 11, Oct. 2, 2005 (Oct. 2, 2005), pp. 1281-1288, XP002399751.
Yulin Chen et al: "On-Chip Synthesis of RNA Aptamer Microarrays for Multiplexed Protein Biosensing with SPR Imaging Measurements", Langmui R. vol. 28. No. 22. Jun. 5, 2012 (Jun. 5, 2012), pp. 8281-8285, XP055391646.
International Search Report corresponding to International Application No. PCT/JP2015/050494 dated Apr. 14, 2015.
Chen et al. "On-Chip Synthesis of RNA Aptamer Microarrays for Multiplexed Protein Biosensing with SPR Imaging Measurements" Langmuir 28(22):8281-8285 (2012).
Extended European Search Report corresponding to European Patent Application No. 15734866.5 (7 pages) (dated Aug. 22, 2017).
GenBank Accession No. AAB90466 LSU ribosomal protein L7AE (rpl7AE) [Archaeoglobus fulgidus DSM 4304] NCBI (2 pages) (2014).
GenBank Accession No. NP_004587 U1 small nuclear ribonucleoprotein A [*Homo sapiens*] NCBI (3 pages) (2017).
Kashida et al. "Three-dimensionally designed protein-responsive RNA devices for cell signaling regulation" Nucleic Acids Research 40(18):9369-9378 (2012).
MiRBase Accession No. MI0000060 "Stem-loop sequence hsa-let-7a-1" miRBase (4 pages) (2003).
MiRBase Accession No. MI0000061 "Stem-loop sequence hsa-let-7a-2" miRBase (4 pages) (2003).

(Continued)

*Primary Examiner* — Robert H Havlin
(74) *Attorney, Agent, or Firm* — Myers Bigel, P.A

(57) ABSTRACT

Interaction with a protein is detected by using an RNA probe containing the following sequences;

(i) a complementary strand sequence to a DNA barcode sequence,
(ii) a sequence of a first stem portion,
(iii) a sequence of a second stem portion complementary to the first stem portion for hybridizing with the first stem portion to form a double-stranded stem, and
(iv) a sequence of a loop portion contained in RNA for linking the first and second stem portions.

7 Claims, 11 Drawing Sheets

Specification includes a Sequence Listing.

(56) References Cited

OTHER PUBLICATIONS

MiRBase Accession No. MI0000062 "Stem-loop sequence hsa-let-7a-3" miRBase (4 pages) (2003).
MiRBase Accession No. MI0000063 "Stem-loop sequence hsa-let-7b" miRBase (3 pages) (2003).
MiRBase Accession No. MI0000064 "Stem-loop sequence hsa-let-7c" miRBase (3 pages) (2003).
MiRBase Accession No. MI0000065 "Stem-loop sequence hsa-let-7d" miRBase (3 pages) (2003).
MiRBase Accession No. MI0000066 "Stem-loop sequence hsa-let-7e" miRBase (3 pages) (2003).
MiRBase Accession No. MI0000067 "Stem-loop sequence hsa-let-7f-1" miRBase (3 pages) (2003).
MiRBase Accession No. MI0000068 "Stem-loop sequence hsa-let-7f-2" miRBase (3 pages) (2003).
MiRBase Accession No. MI0000433 "Stem-loop sequence hsa-let-7g" miRBase (3 pages) (2003).
MiRBase Accession No. MI0000434 "Stem-loop sequence hsa-let-7i" miRBase (3 pages) (2003).
MiRBase Accession No. MI0022909 "Stem-loop sequence mmu-mir-7060" miRBase (2 pages) (2013).
MiRBase Accession No. MI0016052 "Stem-loop sequence hsa-mir-3652" miRBase (1 page) (2010).
MiRBase Accession No. MI0022598 "Stem-loop sequence hsa-mir-6753" miRBase (2 pages) (2013).
MiRBase Accession No. MI0022739 "Stem-loop sequence hsa-mir-6892" miRBase (2 pages) (2013).
Saito et al. "Synthetic human cell fate regulation by protein-driven RNA switches" Nature Communications 2(160):1-8 (2011).
Xu et al. "Design of 240,000 orthogonal 25mer DNA barcode probes" Proceedings of the National Academy of Sciences 106(7):2289-2294 (2009).
Cho et al. "Optimization of aptamer microarray technology for multiple protein targets" Analytica Chemica Acta, 564:82-90 (2006).
Pritchard et al. "MicroRNA profiling: approaches and considerations" Nature Reviews Genetics, 13: 358-369 (2012).

* cited by examiner

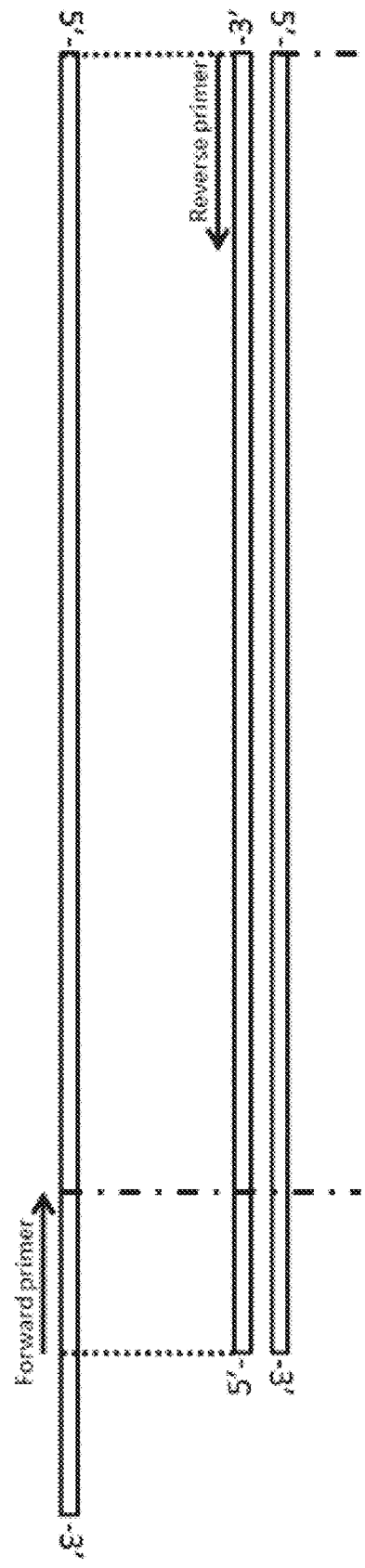

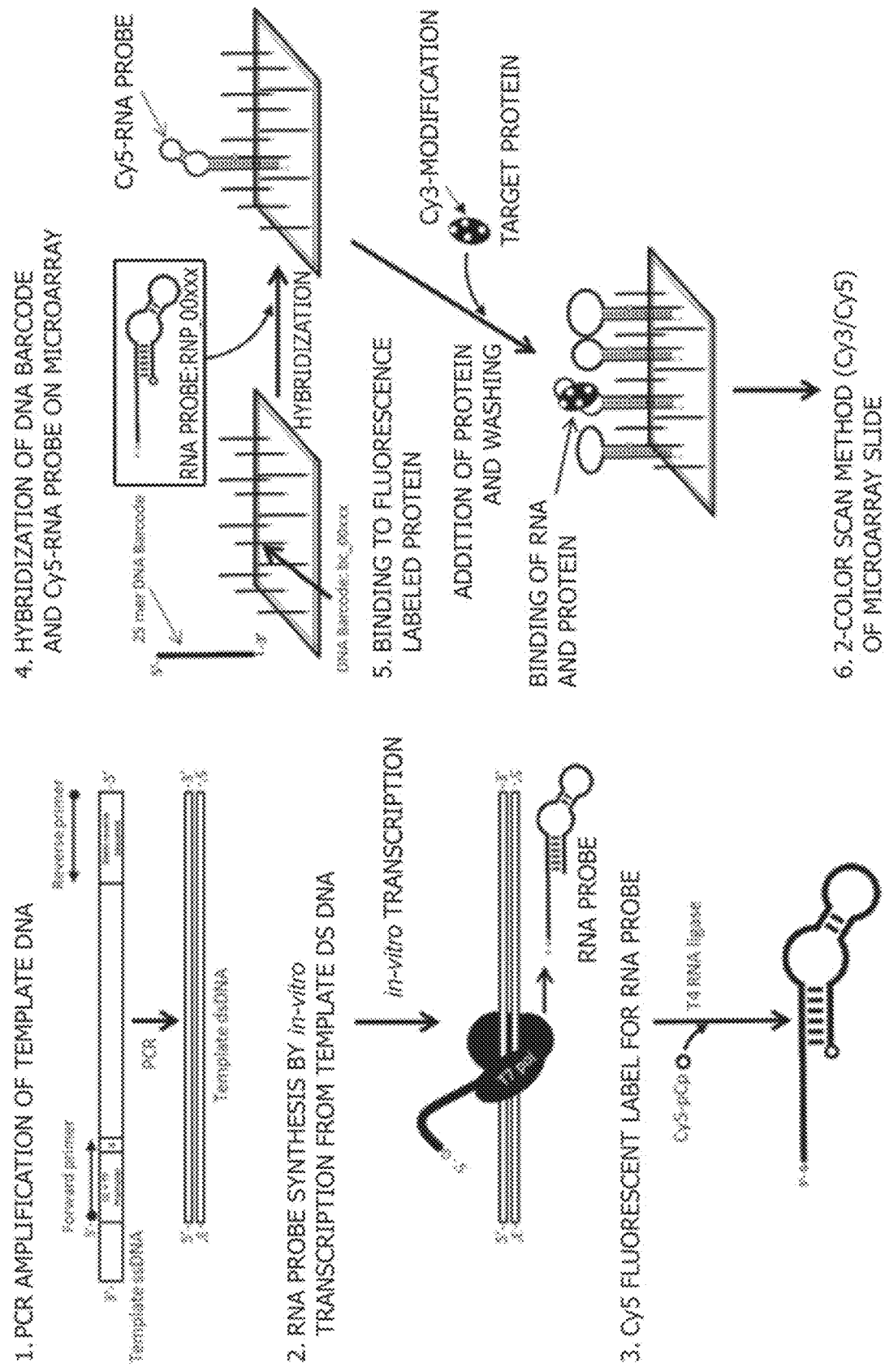

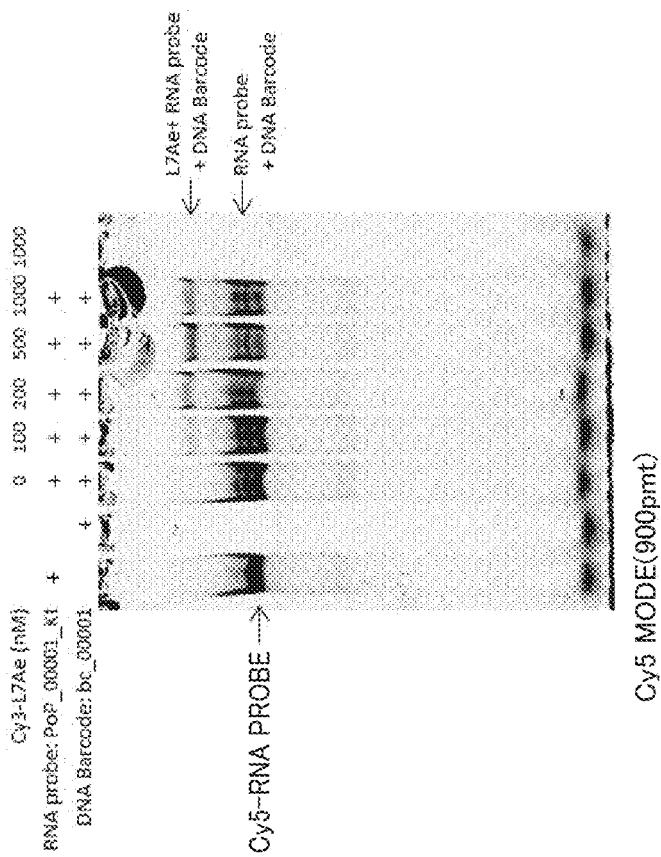
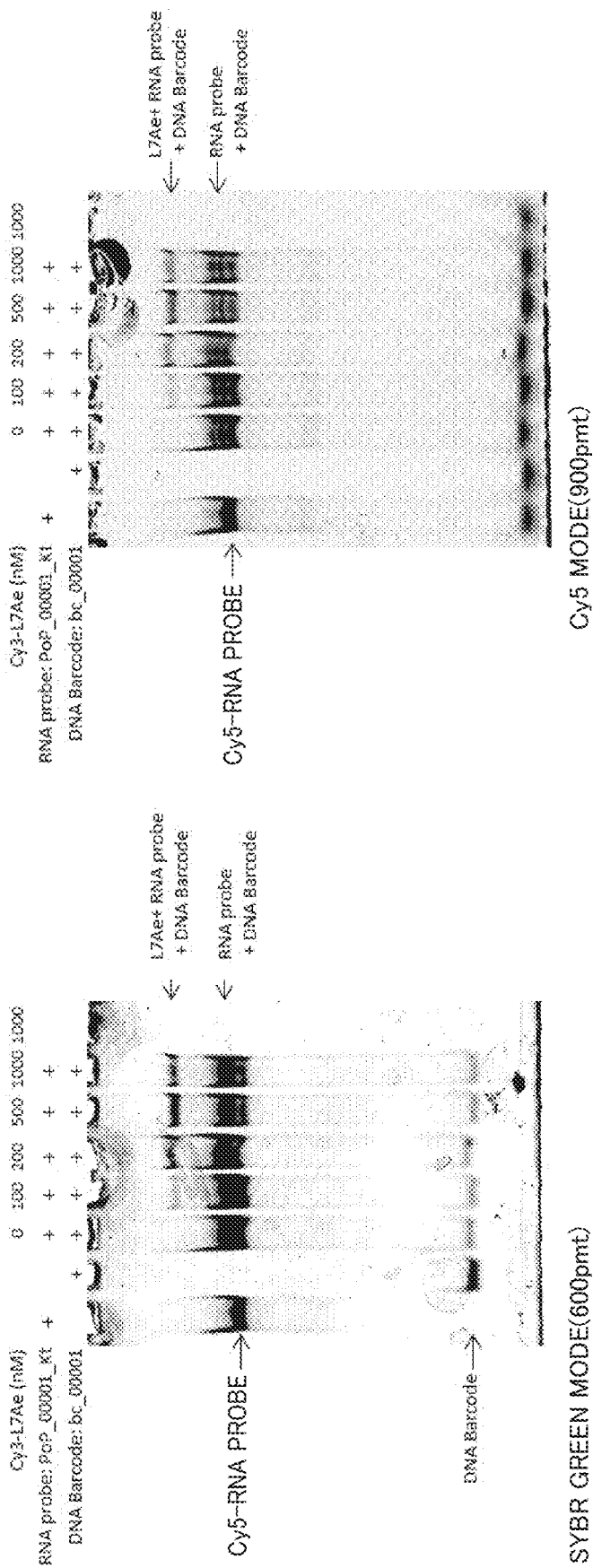
FIG. 4A
FIG. 4B

SEQUENCE LISTING

<160> NUMBER OF SEQ ID NOS: 53

<210> SEQ ID NO 1
<211> LENGTH: 88
<212> TYPE: DNA
<213> ORGANISM: Artificial Sequence
<220> FEATURE:
<223> OTHER INFORMATION: Adjuster Sequence

<400> SEQUENCE: 1
cagagctctc tggctaacta gagaacccac tgcttactgg cttataccaa aatcaacggg    60
actttccaaa atagttatta atagtaat    88

<210> SEQ ID NO 2
<211> LENGTH: 24
<212> TYPE: DNA
<213> ORGANISM: Artificial Sequence
<220> FEATURE:
<223> OTHER INFORMATION: T7 promoter

<400> SEQUENCE: 2
ccgcgctaat acgactcact atag    24

<210> SEQ ID NO 3
<211> LENGTH: 18
<212> TYPE: DNA
<213> ORGANISM: Artificial Sequence
<220> FEATURE:
<223> OTHER INFORMATION: Stem forward sequence

<400> SEQUENCE: 3
ggtgtacgaa gtttcagc    18

<210> SEQ ID NO 4
<211> LENGTH: 17
<212> TYPE: DNA
<213> ORGANISM: Artificial Sequence
<220> FEATURE:
<223> OTHER INFORMATION: Stem reverse sequence

<400> SEQUENCE: 4
gctgaagctt cgtgcac    17

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
ccgcgctaat acgactcact atagg                                             25

<210> SEQ ID NO 6
<211> LENGTH: 17
<212> TYPE: DNA
<213> ORGANISM: Artificial Sequence
<220> FEATURE:
<223> OTHER INFORMATION: PCR primer

<400> SEQUENCE: 6
gtgcacgaag cttcagc                                                      17

<210> SEQ ID NO 7
<211> LENGTH: 180
<212> TYPE: DNA
<213> ORGANISM: Artificial Sequence
<220> FEATURE:
<223> OTHER INFORMATION: RNP_00001

<400> SEQUENCE: 7
gtgcacgaag cttcagcatc acgcccttc gggtcagctg aaacttcgta cacctatgag         60
gacgaatctc ccgcttatac tatagtgagt cgtattagcg cggtaactat tttggaaagt       120
cccgttgatt ttggtataag ccagtaagca gtgggttctc tagttagcca gagagctctg       180

<210> SEQ ID NO 8
<211> LENGTH: 180
<212> TYPE: DNA
<213> ORGANISM: Artificial Sequence
<220> FEATURE:
<223> OTHER INFORMATION: RNP_00002

<400> SEQUENCE: 8
gtgcacgaag cttcagcggg tgatcaccgt tcacacccgc tgaaacttcg tacaccggtc        60
ttgacaaacg tgtgcttgta cctatagtga gtcgtattag cgcggactat tttggaaagt      120
cccgttgatt ttggtataag ccagtaagca gtgggttctc tagttagcca gagagctctg      180

<210> SEQ ID NO 9
<211> LENGTH: 180
<212> TYPE: DNA
<213> ORGANISM: Artificial Sequence
<220> FEATURE:
<223> OTHER INFORMATION: RNP_00003

<400> SEQUENCE: 9
gtgcacgaag cttcagcggg tgatcaccgt tcacacccgg atctcgggtg atcaccgttc        60
acacccgctg aaacttcgta caccgtttat cgggcgtggt gctcgcatac tatagtgagt      120
cgtattagcg cgggtataag ccagtaagca gtgggttctc tagttagcca gagagctctg      180

<210> SEQ ID NO 10
<211> LENGTH: 180
<212> TYPE: DNA
<213> ORGANISM: Artificial Sequence
<220> FEATURE:
<223> OTHER INFORMATION: RNP_00004

<400> SEQUENCE: 10
gtgcacgaag cttcagcggg tgatcaccgt tcacacccgg atctcgggtg atcaccgttc        60
acacccggat ctcgggtgat caccgttcac acccgctgaa acttcgtaca ccccgatgtt    120
gacggactaa tcctgaccta tagtgagtcg tattagcgcg gagttagcca gagagctctg    180

<210> SEQ ID NO 11
<211> LENGTH: 180
<212> TYPE: DNA
<213> ORGANISM: Artificial Sequence
<220> FEATURE:
<223> OTHER INFORMATION: RNP_00005

<400> SEQUENCE: 11
gtgcacgaag cttcagccga tgggtgatcc tcaccggatc tcgatgggtg atcctcaccg     60
ctgaaacttc gtacacctag tagttcagac gccgttaagc gcctatagtg agtcgtatta    120
gcgcgggatt ttggtataag ccagtaagca gtgggttctc tagttagcca gagagctctg    180

<210> SEQ ID NO 12
<211> LENGTH: 180
<212> TYPE: DNA
<213> ORGANISM: Artificial Sequence
<220> FEATURE:
<223> OTHER INFORMATION: RNP_00006

<400> SEQUENCE: 12
gtgcacgaag cttcagctta tgcaccacca cacacacaca cgcgctctct cgctgaaact     60
tcgtacaccc cgtacctaga tacactcaat ttgtctatag tgagtcgtat tagcgcgggt    120
cccgttgatt ttggtataag ccagtaagca gtgggttctc tagttagcca gagagctctg    180

<210> SEQ ID NO 13
<211> LENGTH: 180
<212> TYPE: DNA
<213> ORGANISM: Artificial Sequence
<220> FEATURE:
<223> OTHER INFORMATION: RNP_00007

<400> SEQUENCE: 13
gtgcacgaag cttcagcaca cacacacaca cacacacaca cagctgaaac ttcgtacacc     60
ggggttccgt tttacattcc aggaactata gtgagtcgta ttagcgcggt tttggaaagt    120
cccgttgatt ttggtataag ccagtaagca gtgggttctc tagttagcca gagagctctg    180

<210> SEQ ID NO 14
<211> LENGTH: 180
<212> TYPE: DNA
<213> ORGANISM: Artificial Sequence
<220> FEATURE:
<223> OTHER INFORMATION: RNP_00008

<400> SEQUENCE: 14
gtgcacgaag cttcagcatg acgccctttc gggcagctga aacttcgtac acctatcccg     60
tgaagcttga gtggaatcct atagtgagtc gtattagcgc ggataactat tttggaaagt    120
cccgttgatt ttggtataag ccagtaagca gtgggttctc tagttagcca gagagctctg    180

<210> SEQ ID NO 15
<211> LENGTH: 180
<212> TYPE: DNA
<213> ORGANISM: Artificial Sequence
<220> FEATURE:
<223> OTHER INFORMATION: RNP_00009

<400> SEQUENCE: 15
gtgcacgaag cttcagcggt gcaatgtccc gaaggactcg ctgaaacttc gtacaccctg     60
acgtgtgagg cgctagagca tactatagtg agtcgtatta gcgcggctat tttggaaagt        120
cccgttgatt ttggtataag ccagtaagca gtgggttctc tagttagcca gagagctctg        180

<210> SEQ ID NO 16
<211> LENGTH: 180
<212> TYPE: DNA
<213> ORGANISM: Artificial Sequence
<220> FEATURE:
<223> OTHER INFORMATION: RNP_00010

<400> SEQUENCE: 16
gtgcacgaag cttcagcggt gcaatgtccc gaaggactcg ctgaaacttc gtacaccggt         60
atggcacgcc taatctggac acctatagtg agtcgtatta gcgcggctat tttggaaagt        120
cccgttgatt ttggtataag ccagtaagca gtgggttctc tagttagcca gagagctctg        180

<210> SEQ ID NO 17
<211> LENGTH: 180
<212> TYPE: DNA
<213> ORGANISM: Artificial Sequence
<220> FEATURE:
<223> OTHER INFORMATION: RNP_00011

<400> SEQUENCE: 17
gtgcacgaag cttcagcgcc gtaatgtccc gaaggactcg ctgaaacttc gtacaccgga         60
tgcatgatct agggcctcgt ctctatagtg agtcgtatta gcgcggctat tttggaaagt        120
cccgttgatt ttggtataag ccagtaagca gtgggttctc tagttagcca gagagctctg        180

<210> SEQ ID NO 18
<211> LENGTH: 180
<212> TYPE: DNA
<213> ORGANISM: Artificial Sequence
<220> FEATURE:
<223> OTHER INFORMATION: RNP_00012

<400> SEQUENCE: 18
gtgcacgaag cttcagcgcc gtaatgtccc gaaggactcg ctgaaacttc gtacaccgag         60
gtctttcatg cgtatagtca cactatagtg agtcgtatta gcgcggctat tttggaaagt        120
cccgttgatt ttggtataag ccagtaagca gtgggttctc tagttagcca gagagctctg        180

<210> SEQ ID NO 19
<211> LENGTH: 180
<212> TYPE: DNA
<213> ORGANISM: Artificial Sequence
<220> FEATURE:
<223> OTHER INFORMATION: RNP_00013

<400> SEQUENCE: 19
gtgcacgaag cttcagcgga gtgcaatgct gaaacttcgt acaccgattc aatatgtgtc         60
gtctatcctc ctatagtgag tcgtattagc gcggtactat taataactat tttggaaagt        120
cccgttgatt ttggtataag ccagtaagca gtgggttctc tagttagcca gagagctctg        180

<210> SEQ ID NO 20
<211> LENGTH: 180
<212> TYPE: DNA
<213> ORGANISM: Artificial Sequence
<220> FEATURE:
<223> OTHER INFORMATION: RNP_00014

<400> SEQUENCE: 20

```
gtgcacgaag cttcagcgga gtgcaatgct gaaacttcgt acaccggtaa ctgcgcatag      60
ttggctctat ctatagtgag tcgtattagc gcggtactat taataactat tttggaaagt     120
cccgttgatt ttggtataag ccagtaagca gtgggttctc tagttagcca gagagctctg     180
```

<210> SEQ ID NO 21
<211> LENGTH: 180
<212> TYPE: DNA
<213> ORGANISM: Artificial Sequence
<220> FEATURE:
<223> OTHER INFORMATION: RNP_00015

<400> SEQUENCE: 21

```
gtgcacgaag cttcagcgga ccgtaatgct gaaacttcgt acaccgcgtt taaggtcaca      60
tcgcatgaat ctatagtgag tcgtattagc gcggtactat taataactat tttggaaagt     120
cccgttgatt ttggtataag ccagtaagca gtgggttctc tagttagcca gagagctctg     180
```

<210> SEQ ID NO 22
<211> LENGTH: 180
<212> TYPE: DNA
<213> ORGANISM: Artificial Sequence
<220> FEATURE:
<223> OTHER INFORMATION: RNP_00016

<400> SEQUENCE: 22

```
gtgcacgaag cttcagcgga ccgtaatgct gaaacttcgt acaccgcccg ggaagtgtga      60
ggatataccc ctatagtgag tcgtattagc gcggtactat taataactat tttggaaagt     120
cccgttgatt ttggtataag ccagtaagca gtgggttctc tagttagcca gagagctctg     180
```

<210> SEQ ID NO 23
<211> LENGTH: 180
<212> TYPE: DNA
<213> ORGANISM: Artificial Sequence
<220> FEATURE:
<223> OTHER INFORMATION: RNP_00017

<400> SEQUENCE: 23

```
gtgcacgaag cttcagctgg gatacaaatg ttcagtttgg atgatgagaa tgaggcaagt      60
agtggagaca gctgaaactt cgtacaccgc tcttaaaact ggtatcacct gacctatagt     120
gagtcgtatt agcgcggaag ccagtaagca gtgggttctc tagttagcca gagagctctg     180
```

<210> SEQ ID NO 24
<211> LENGTH: 180
<212> TYPE: DNA
<213> ORGANISM: Artificial Sequence
<220> FEATURE:
<223> OTHER INFORMATION: RNP_00018

<400> SEQUENCE: 24

```
gtgcacgaag cttcagcata gttatctccc agtggtgggt gtgaccctaa aactatgctg      60
aaacttcgta caccgggtgg ttagtgattt gcccgtcacc tatagtgagt cgtattagcg     120
cgggttgatt ttggtataag ccagtaagca gtgggttctc tagttagcca gagagctctg     180
```

<210> SEQ ID NO 25
<211> LENGTH: 180
<212> TYPE: DNA
<213> ORGANISM: Artificial Sequence
<220> FEATURE:
<223> OTHER INFORMATION: RNP_00019

<400> SEQUENCE: 25

```
gtgcacgaag cttcagcaca gttatctccc ttgatgtaat tctaaactat gctgaaactt    60
cgtacaccta gttggtgggt ttccctaccg tgtctatagt gagtcgtatt agcgcggagt   120
cccgttgatt ttggtataag ccagtaagca gtgggttctc tagttagcca gagagctctg   180
```

<210> SEQ ID NO 26
<211> LENGTH: 180
<212> TYPE: DNA
<213> ORGANISM: Artificial Sequence
<220> FEATURE:
<223> OTHER INFORMATION: RNP_00020

<400> SEQUENCE: 26

```
gtgcacgaag cttcagcata gttatcccat agcagggcag agccccaaac tatgctgaaa    60
cttcgtacac cggtacagta agtgagaatc ctctctctat agtgagtcgt attagcgcgg   120
cccgttgatt ttggtataag ccagtaagca gtgggttctc tagttagcca gagagctctg   180
```

<210> SEQ ID NO 27
<211> LENGTH: 180
<212> TYPE: DNA
<213> ORGANISM: Artificial Sequence
<220> FEATURE:
<223> OTHER INFORMATION: RNP_00021

<400> SEQUENCE: 27

```
gtgcacgaag cttcagcata gttatcttcc gaggggcaac atcactgccc tgaaaccacg    60
ctgaaacttc gtacaccggt tctaagttta gcgtagccgg ttctatagtg agtcgtatta   120
gcgcgggatt ttggtataag ccagtaagca gtgggttctc tagttagcca gagagctctg   180
```

<210> SEQ ID NO 28
<211> LENGTH: 180
<212> TYPE: DNA
<213> ORGANISM: Artificial Sequence
<220> FEATURE:
<223> OTHER INFORMATION: RNP_00022

<400> SEQUENCE: 28

```
gtgcacgaag cttcagcagt taactcccag ggtgtaactc taaaccgctg aaacttcgta    60
caccctttag gtgggtgcga ttgccagttc tatagtgagt cgtattagcg cggggaaagt   120
cccgttgatt ttggtataag ccagtaagca gtgggttctc tagttagcca gagagctctg   180
```

<210> SEQ ID NO 29
<211> LENGTH: 180
<212> TYPE: DNA
<213> ORGANISM: Artificial Sequence
<220> FEATURE:
<223> OTHER INFORMATION: RNP_00023

<400> SEQUENCE: 29

```
gtgcacgaag cttcagcata gttacctcct tgtgggcaaa atccctgccc taaaactatg    60
ctgaaacttc gtacaccgcc acctaacacg cgatgatat tgctatagtg agtcgtatta    120
gcgcgggatt ttggtataag ccagtaagca gtgggttctc tagttagcca gagagctctg   180
```

<210> SEQ ID NO 30
<211> LENGTH: 180
<212> TYPE: DNA
<213> ORGANISM: Artificial Sequence
<220> FEATURE:
<223> OTHER INFORMATION: RNP_00024

```
<400> SEQUENCE: 30
gtgcacgaag cttcagcata gtgatctcct tgggtgtcct cctcaactat gctgaaactt      60
cgtacaccgc tattacgagc gcttggatcc cgtctatagt gagtcgtatt agcgcggagt     120
cccgttgatt ttggtataag ccagtaagca gtgggttctc tagttagcca gagagctctg     180

<210> SEQ ID NO 31
<211> LENGTH: 180
<212> TYPE: DNA
<213> ORGANISM: Artificial Sequence
<220> FEATURE:
<223> OTHER INFORMATION: RNP_00025

<400> SEQUENCE: 31
gtgcacgaag cttcagcata gttatctcct gaacagggta aaatcactac cccacaacta      60
tgctgaaact tcgtacacct atgttgtgcc ttacgcctcg attactatag tgagtcgtat     120
tagcgcggtt ttggtataag ccagtaagca gtgggttctc tagttagcca gagagctctg     180

<210> SEQ ID NO 32
<211> LENGTH: 180
<212> TYPE: DNA
<213> ORGANISM: Artificial Sequence
<220> FEATURE:
<223> OTHER INFORMATION: RNP_00026

<400> SEQUENCE: 32
gtgcacgaag cttcagcata gttatctcca agatggggta tgaccctaaa actatgctga      60
aacttcgtac accttaaccg aactgacggc catcaaggct atagtgagtc gtattagcgc     120
ggcgttgatt ttggtataag ccagtaagca gtgggttctc tagttagcca gagagctctg     180

<210> SEQ ID NO 33
<211> LENGTH: 180
<212> TYPE: DNA
<213> ORGANISM: Artificial Sequence
<220> FEATURE:
<223> OTHER INFORMATION: RNP_00027

<400> SEQUENCE: 33
gtgcacgaag cttcagcaca gttatctcct gtaccgggtg gtatcataga ccctcaaact      60
gtgctgaaac ttcgtacacc gggtacatgc gccttactcc ttgtgctata gtgagtcgta     120
ttagcgcggt ttggtataag ccagtaagca gtgggttctc tagttagcca gagagctctg     180

<210> SEQ ID NO 34
<211> LENGTH: 180
<212> TYPE: DNA
<213> ORGANISM: Artificial Sequence
<220> FEATURE:
<223> OTHER INFORMATION: RNP_00028

<400> SEQUENCE: 34
gtgcacgaag cttcagcgca gttatctcca cagcgggcaa tgtcacaacc cgaccaacag      60
cgctgaaact tcgtacacct tctattctaa gccggcggtc atatctatag tgagtcgtat     120
tagcgcggtt ttggtataag ccagtaagca gtgggttctc tagttagcca gagagctctg     180

<210> SEQ ID NO 35
<211> LENGTH: 180
<212> TYPE: DNA
<213> ORGANISM: Artificial Sequence
<220> FEATURE:
<223> OTHER INFORMATION: RNP_00029
```

```
<400> SEQUENCE: 35
gtgcacgaag cttcagcggg ctccttgccc gctgaaactt cgtacaccgc ttgatgcttt      60
acaagatcgc gttctatagt gagtcgtatt agcgcggtat taataactat tttggaaagt     120
cccgttgatt ttggtataag ccagtaagca gtgggttctc tagttagcca gagagctctg     180

<210> SEQ ID NO 36
<211> LENGTH: 103
<212> TYPE: DNA
<213> ORGANISM: Artificial Sequence
<220> FEATURE:
<223> OTHER INFORMATION: Kt

<400> SEQUENCE: 36
gtgcacgaag cttcagcatc acgcccttc gggtcagctg aaacttcgta cacctatgag       60
gacgaatctc ccgcttatac tatagtgagt cgtattagcg cgg                        103

<210> SEQ ID NO 37
<211> LENGTH: 102
<212> TYPE: DNA
<213> ORGANISM: Artificial Sequence
<220> FEATURE:
<223> OTHER INFORMATION: dKt

<400> SEQUENCE: 37
tccgggaata tagcgccatg acgcccttc gggcaggcac tatattccca aactatcccg        60
tgaagcttga gtggaatcct atagtgagtc gtattagcgc gg                         102

<210> SEQ ID NO 38
<211> LENGTH: 106
<212> TYPE: DNA
<213> ORGANISM: Artificial Sequence
<220> FEATURE:
<223> OTHER INFORMATION: U1A2

<400> SEQUENCE: 38
tccgggaata tagcgccggt gcaatgtccc gaaggactcg gcactatatt cccaaacggt       60
atggcacgcc taatctggac acctatagtg agtcgtatta gcgcgg                    106

<210> SEQ ID NO 39
<211> LENGTH: 106
<212> TYPE: DNA
<213> ORGANISM: Artificial Sequence
<220> FEATURE:
<223> OTHER INFORMATION: dU1A2

<400> SEQUENCE: 39
tccgggaata tagcgccgcc gtaatgtccc gaaggactcg gcactatatt cccaaacgga       60
tgcatgatct agggcctcgt ctctatagtg agtcgtatta gcgcgg                    106

<210> SEQ ID NO 40
<211> LENGTH: 94
<212> TYPE: DNA
<213> ORGANISM: Artificial Sequence
<220> FEATURE:
<223> OTHER INFORMATION: U1A

<400> SEQUENCE: 40
tccgggaata tagcgccgga gtgcaatggc actatattcc caaacggtaa ctgcgcatag       60
ttggctctat ctatagtgag tcgtattagc gcgg                                  94
```

<210> SEQ ID NO 41
<211> LENGTH: 94
<212> TYPE: DNA
<213> ORGANISM: Artificial Sequence
<220> FEATURE:
<223> OTHER INFORMATION: dU1A

<400> SEQUENCE: 41
tccgggaata tagcgccgga ccgtaatggc actatattcc caaacgcccg ggaagtgtga    60
ggatataccc ctatagtgag tcgtattagc gcgg                                94

<210> SEQ ID NO 42
<211> LENGTH: 130
<212> TYPE: DNA
<213> ORGANISM: Artificial Sequence
<220> FEATURE:
<223> OTHER INFORMATION: hsa-let-7a-1

<400> SEQUENCE: 42
gtgcacgaag cttcagcata gttatctccc agtggtgggt gtgaccctaa aactatgctg    60
aaacttcgta caccgggtgg ttagtgattt gcccgtcacc tatagtgagt cgtattagcg   120
cggagctctg                                                          130

<210> SEQ ID NO 43
<211> LENGTH: 130
<212> TYPE: DNA
<213> ORGANISM: Artificial Sequence
<220> FEATURE:
<223> OTHER INFORMATION: hsa-let-7a-2

<400> SEQUENCE: 43
gtgcacgaag cttcagcaca gttatctccc ttgatgtaat tctaaactat gctgaaactt    60
cgtacaccta gttggtgggt ttccctaccg tgtctatagt gagtcgtatt agcgcggcca   120
gagagctctg                                                          130

<210> SEQ ID NO 44
<211> LENGTH: 130
<212> TYPE: DNA
<213> ORGANISM: Artificial Sequence
<220> FEATURE:
<223> OTHER INFORMATION: hsa-let-7a-3

<400> SEQUENCE: 44
gtgcacgaag cttcagcata gttatcccat agcagggcag agcccaaac tatgctgaaa     60 cttcgtacac cggtacagta agtgagaatc ctctctctat agtgagtcgt attagcgcgg   120
gagagctctg                                                          130

<210> SEQ ID NO 45
<211> LENGTH: 130
<212> TYPE: DNA
<213> ORGANISM: Artificial Sequence
<220> FEATURE:
<223> OTHER INFORMATION: hsa-let-7b

<400> SEQUENCE: 45
gtgcacgaag cttcagcata gttatcttcc gaggggcaac atcactgccc tgaaaccacg    60
ctgaaacttc gtacaccggt tctaagttta gcgtagccgg ttctatagtg agtcgtatta   120
gcgcggtctg                                                          130

```
<210> SEQ ID NO 46
<211> LENGTH: 130
<212> TYPE: DNA
<213> ORGANISM: Artificial Sequence
<220> FEATURE:
<223> OTHER INFORMATION: hsa-let-7c

<400> SEQUENCE: 46
gtgcacgaag cttcagcagt taactcccag ggtgtaactc taaaccgctg aaacttcgta      60
caccctttag gtgggtgcga ttgccagttc tatagtgagt cgtattagcg cggttagcca     120
gagagctctg                                                            130

<210> SEQ ID NO 47
<211> LENGTH: 130
<212> TYPE: DNA
<213> ORGANISM: Artificial Sequence
<220> FEATURE:
<223> OTHER INFORMATION: hsa-let-7d

<400> SEQUENCE: 47
gtgcacgaag cttcagcata gttacctcct tgtgggcaaa atccctgccc taaaactatg      60
ctgaaacttc gtacaccgcc accttaacac gcgatgatat tgctatagtg agtcgtatta     120
gcgcggtctg                                                            130

<210> SEQ ID NO 48
<211> LENGTH: 130
<212> TYPE: DNA
<213> ORGANISM: Artificial Sequence
<220> FEATURE:
<223> OTHER INFORMATION: hsa-let-7e

<400> SEQUENCE: 48
gtgcacgaag cttcagcata gtgatctcct tgggtgtcct cctcaactat gctgaaactt      60
cgtacaccgc tattacgagc gcttggatcc cgtctatagt gagtcgtatt agcgcggcca     120
gagagctctg                                                            130

<210> SEQ ID NO 49
<211> LENGTH: 130
<212> TYPE: DNA
<213> ORGANISM: Artificial Sequence
<220> FEATURE:
<223> OTHER INFORMATION: hsa-let-7f-1

<400> SEQUENCE: 49
gtgcacgaag cttcagcata gttatctcct gaacagggta aaatcactac cccacaacta      60
tgctgaaact tcgtacacct atgttgtgcc ttacgcctcg attactatag tgagtcgtat     120
tagcgcggtg                                                            130

<210> SEQ ID NO 50
<211> LENGTH: 130
<212> TYPE: DNA
<213> ORGANISM: Artificial Sequence
<220> FEATURE:
<223> OTHER INFORMATION: hsa-let-7f-2

<400> SEQUENCE: 50
gtgcacgaag cttcagcata gttatctcca agatggggta tgaccctaaa actatgctga      60
aacttcgtac accttaaccg aactgacggc catcaaggct atagtgagtc gtattagcgc     120
gggagctctg                                                            130
```

```
<210> SEQ ID NO 51
<211> LENGTH: 130
<212> TYPE: DNA
<213> ORGANISM: Artificial Sequence
<220> FEATURE:
<223> OTHER INFORMATION: hsa-let-7g

<400> SEQUENCE: 51
gtgcacgaag cttcagcaca gttatctcct gtaccgggtg gtatcataga ccctcaaact    60
gtgctgaaac ttcgtacacc gggtacatgc gccttactcc ttgtgctata gtgagtcgta   120
ttagcgcggg                                                          130

<210> SEQ ID NO 52
<211> LENGTH: 130
<212> TYPE: DNA
<213> ORGANISM: Artificial Sequence
<220> FEATURE:
<223> OTHER INFORMATION: hsa-let-7i

<400> SEQUENCE: 52
gtgcacgaag cttcagcgca gttatctcca cagcgggcaa tgtcacaacc cgaccaacag    60
cgctgaaact tcgtacacct tctattctaa gccggcggtc atatctatag tgagtcgtat   120
tagcgcggtg                                                          130

<210> SEQ ID NO 53
<211> LENGTH: 130
<212> TYPE: DNA
<213> ORGANISM: Artificial Sequence
<220> FEATURE:
<223> OTHER INFORMATION: consensus

<400> SEQUENCE: 53
gtgcacgaag cttcagcggg ctccttgccc gctgaaactt cgtacaccgc ttgatgcttt    60
acaagatcgc gttctatagt gagtcgtatt agcgcgggca gtgggttctc tagttagcca   120
gagagctctg                                                          130
```

RNA MICROARRAY FOR DETECTING INTERACTION BETWEEN PROTEIN AND RNA CONTAINING A HIGHER-ORDER STRUCTURE

RELATED APPLICATIONS

This application is a divisional of U.S. application Ser. No. 15/110,516, which is a 35 U.S.C. § 371 national phase application of PCT Application PCT/JP2015/050494 filed Jan. 9, 2015, which claims priority to Japanese Application No. 2014-003734 filed Jan. 10, 2014. The entire contents of each are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-324DV_ST25.txt, 17,106 bytes in size, generated on Aug. 29, 2019, and filed via EFS-Web, is provided of a paper copy. This Sequence Listing is hereby incorporated by reference into the specification for its disclosures.

FIELD AND BACKGROUND OF THE INVENTION

The present invention relates to an RNA microarray for detecting Pre-miRNA interacting with a protein.

An RNA-protein (RNP) interaction is a major control factor in gene expression. It has been reported that a specific RNP interaction determines a cell fate and a disease (Non Patent Literature 1).

For example, Lin28A protein binds to a Pre-let7 miRNA at two sites, i.e., two loop regions of a loop-stem-loop structure (Non Patent Literature 2). Likewise, RNA having a chain length of 10 bases or more has a self-folding property for a three-dimensional structure, which is more complicated than DNA. In most cases, RNA having such a structure is inevitably required for specific interaction with a protein.

Owing to recent RNA-protein interaction analysis, studies for identifying a sequence having high binding-affinity to a known RNA-binding protein from random sequences having about 7 to 9 bases have been globally conducted; however, it was confirmed that the proteins which bind to these short RNA sequences are mostly housekeeping genes and rarely have a property of resulting in a specific response (Non Patent Literature 3). Large-scale analysis for elucidating the interactions bet peen the RNA sequence, which has a structure formed of 10 bases or more and potentially serves as a cell fate control factor, and a protein, has not yet been performed.

CITATION LIST

Non Patent Literature

[Non Patent Literature 1] Keene, J. D. (2007) Nature reviews. Genetics 8, 533-543.
[Non Patent Literature 2] Nam, Y., Chen, C., Gregory, R. I., et al. (2011) Cell 147, 1080-1091.
[Non Patent Literature 3] Ray, D., Kazan, H., Cook, K. B., et al. (2013) Nature 499, 172-177.

SUMMARY OF INVENTION

Technical Problem

It has been desired to develop a method for exhaustively analyzing the interactions between a protein and RNA containing a higher-order structure.

Solution to Problem

The present inventors conducted intensive studies in consideration of the aforementioned problems. They exhaustively prepared RNA probes having a loop region of the Pre-miRNA secondary structures estimated by a conventional method, and found that Pre-miRNA interacting with a target protein can be identified by an RNA microarray having these RNA probes. Based on the finding, the present invention has been accomplished.

More specifically, the present invention provides the following:

[1] An RNA probe containing the following sequences,
(i) a complementary strand sequence to a DNA barcode sequence,
(ii) a sequence of a first stem portion,
(iii) a sequence of a second stem portion, which is complementary to the first stem portion for hybridizing with the first stem portion to form a double-stranded stem, and
(iv) a sequence of a loop portion for linking the first and second stem portions.

[2] The RNA probe according to [1], in which the sequence of the loop portion is a sequence of a loop portion contained in Pre-miRNA.

[3] The RNA probe according to [1] or [2], having a fluorescence-labeled 3' end.

[4] The RNA probe according to [1] or [3], in which the Pre-miRNA is human or mouse Pre-miRNA.

[5] A method for producing an RNA microarray for use in detecting a protein which binds to RNA, including hybridizing a slide having a DNA barcode sequence attached thereto and the RNA probe according to any one of [1] to [4].

[6] An RNA microarray produced by hybridizing a slide having a DNA barcode sequence attached thereto and the RNA probe according to any one of [1] to [14].

[7] The RNA microarray according to [6], having two types or more RNA probes different in the sequence (i) and identical in sequences (ii), (iii) and (iv).

[8] A method for detecting RNA which binds to a protein, having the following steps:
(1) a step of bringing the RNA microarray according to [6] or [7] and a slide having a DNA barcode sequence attached thereto and no RNA probe hybridized therewith, into contact with a fluorescence-labeled target protein,
(2) a step of identifying an RNA probe and a DNA barcode sequence, which were bound to the target protein, and
(3) a step of obtaining an RNA probe by eliminating the RNA probe having a complementary strand corresponding to the DNA barcode sequence and identified in step (2) from the RNA probes identified in stop (2), and detecting RNA containing a sequence of a loop portion contained in the RNA probe obtained, as the RNA which hinds to the target protein,

[9] The method according to [8], in which the RNA is Pre-miRNA.

[10] A method for detecting RNA which binds to a protein, having the following steps:

(1) a step of bringing the RNA probe according to any one of [1] to [4] into contact with a target protein, (2) a step of isolating the target protein obtained in step (1) while maintaining binding to the RNA probe, (3) a step of extracting the RNA probe front the target protein obtained in step (2), (4) a step of bringing the RNA probe obtained in step (3) into contact with the slide having a DNA barcode sequence attached thereto, (5) a step of identifying the RNA probe hybridized with the slide having the DNA barcode sequence attached thereto, and (6) a step of detecting RNA containing the sequence (iv) contained in the RNA probe identified in step (5) as the RNA which binds to the target protein.

[11] The method according to [10], in which the RNA is Pre-miRNA.

Advantageous Effects of Invention

According to the present invention, owing to use of a DNA barcode sequence, RNA can be disposed at a desired position on a slide while using a conventional microarray technique. Because of this, RNA interacting with a protein can be exhaustively identified. The method according to the present invention is particularly advantageous in that a protein interacting with the loop region can be detected while maintaining the secondary structure of the loop region of Pre-miRNA.

In addition, in the present invention, to prevent generation of noise due to binding of a target protein to a DNA barcode sequence, the DNA barcode sequence(s) to which the protein binds, is eliminated from the detection results. In this manner, the secondary structure of RNA to which a desired protein binds can be solely and accurately detected.

BRIEF DESCRIPTION OF DRAWINGS

FIGS. 1A-1C are pattern diagrams showing the design of template DNA to be transcribed into an RNA probe.

FIG. 3 is a pattern diagram of a protocol for a method for preparing an RNA array.

FIGS. 4A-4B show the results of the interaction of PoP_00001_Kt with Cy3-L7Ae checked by gel shift assay.

DESCRIPTION OF EMBODIMENT

Figure 2A:
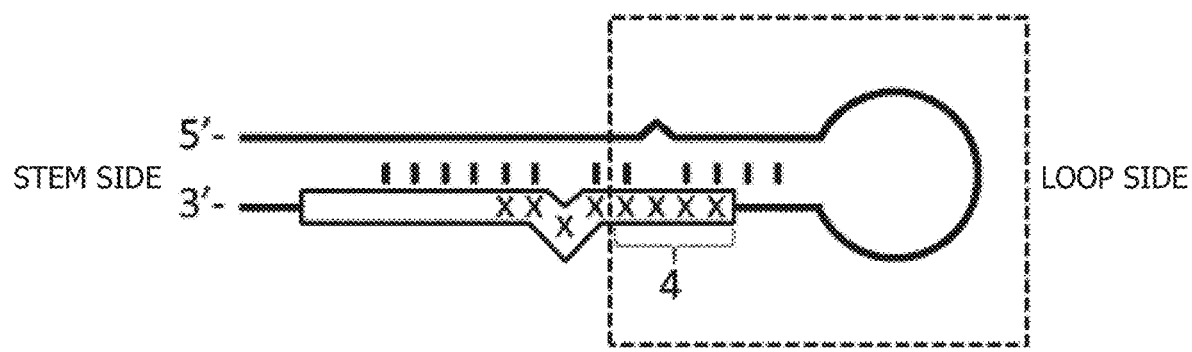
FIGS. 2A-2B are pattern diagrams showing the design of a loop region of Pre-miRNA.

Now, the present invention will be more specifically described by way or embodiments; however, the embodiments should not be construed as limiting the present invention.

The present invention provides an RNA probe containing the following sequences:

(i) a complementary strand sequence to a DNA barcode sequence, (ii) a sequence of a first stem portion, (iii) a sequence of a second stem portion, which is complementary to the first stem portion, for hybridizing with the first stem portion to form a double-stranded stem, and (iv) a sequence of a loop portion contained in RNA for linking the first and second stem portions.

The RNA probe of the present invention refers to a nucleic acid molecule having a sequence that can be interact with a target substance and more preferably RNA. In the present invention, the target substance is preferably a protein. The RNA probe may be labeled with a radioactive isotope, digoxigenin (DIG), a fluorescent dye (for example, FITC, PE, Cy3 and Cy5) or a molecule (antigen) such as biotin for detection, by integrating it into the probe. The RNA probe can be labeled by a method of integrating a previously-labeled nucleic acid into a probe during probe synthesis; for example, by labeling a nucleoside C group (cytidine group), which is complementary to a G group (guanine group), arranged at the 5' side of the first stem portion (e.g., 3', 5'-cytidine bisphosphate-Cy5 (pCp-Cy5)) and then integrating cytidine into the 3' end.

In the present invention, the RNA probe, if the sequence thereof is determined as mentioned above, can be synthesized by those skilled in the art in accordance with any genetic engineering method known in the art. The RNA probe may be preferably prepared by transcribing the DNA synthesized by an outsourcer specialized in synthesis. For transcribing DNA into RNA, DNA containing the sequence of the RNA probe may have a promoter sequence. Examples of a preferable promoter sequence include, but are not particularly limited to, a T7 promoter sequence. When a T7 promoter sequence is used, RNA can be transcribed from DNA having a desired RNA probe sequence by use of, for example, MEGA shortscript (trade mark) T7 Transcription Kit provided by Life Technologies. In the present invention, RNA may be composed not only of adenine, guanine, cytosine and uracil, but also modified RNAs. Examples of a modified RNA include pseudouridine, 5-methylcytosine, 5-methyluridine, 2'-O-methyluridine, 2-thiouridine and N6-methyladenosine.

In the present invention, for preparing a microarray having RNA probes, it is preferable to prepare various types of RNA probes simultaneously, and it is preferable to conduct preparation using Oligonucleotide Library Synthesis technology containing RNA probes efficiently. In this case, in order to synthesize DNA containing all RNA probe sequences within a specific base length (desirably 200 bases or less, for example, 180 bases), a regulatory sequence may be contained other than the RNA probes and the promoter sequence. The regulatory sequence may be any sequence as long as it is not complementary to functional sequences such as a promoter Sequence and a poly A sequence, and other sequences. For example, a sequence having a desired base length and appropriately selected from sequences represented by SEQ ID No. 1, may be used. In the present invention, although it is not particularly limited, preparation of the Oligonucleotide Library Synthesis can be outsourced to Agilent Technologies.

The DNA barcode sequence of the present invention is a sequence called, e.g., a tag (National Publication of International Patent Application No. 10-507357, National Publication of International Patent Application 2002-518060); a zip code (National Publication of International Patent Application 2001-519648) or an orthonormal sequence (Japanese Patent Laid-Open No. 2002-181813); or a barcode sequence (Xu, Q., Schlabach, M. R., Hannon, G. J. et al. (2009) PNAS 106, 2289-2294). The DNA barcode sequence desirably has a low cross-reactivity (cross hybridization). The DNA barcode sequence is a sequence having 20 to 30 bases and preferably 25 bases. In the present invention, a microarray is prepared by spotting the DNA barcode sequence on an immobilization support such as microbeads or a glass slide, and then, an RNA probe is allowed to hybridize with the microarray. In this manner, the RNA probe is positioned at a specific site. For this purpose, it is preferable that the RNA probe have a complementary strand sequence to the DNA barcode sequence.

In the present invention, the stem refers to a site at which a nucleic acid sequence and a complementary sequence thereto form a double helix structure. The first stem refers to a nucleic acid sequence and the second stem refers to a sequence complementary to the first stem. In the present invention, "complementary" means the ability of two nucleic acid sequences to hybridize. Since it is sufficient that two sequences hybridize with each other, "the second stem is complementary to the first stem" herein means that it is sufficient that the second stem portion has a sequence complementarily of at least 70%, 75%, 80%, 85%, 90%, 95%, 99% or 100% to the first stem portion. SEQ 1D No. 3 is mentioned as an example of the first stem portion; whereas SEQ No. 4 is mentioned as an example of the second stem portion. In the present invention, it is preferable that fluorescent dye-labeled cytidine (pCp-Cy5) be added to the 3' end of an RNA probe as mentioned above. Thus, it is desirable that a guanine base be added to the 5' end of the first stem. If a fluorescent dye-label is tagged to a base except cytidine, it is desirable that a base making; a pair with the base be selected and added to the 5' end of the first stem.

In the present invention, "two stem portions are linked" means that the 3' end of the first stem is linked to the 5' end of the second stem. The sequence to be linked may be RNA consisting of any sequence as long as it is a sequence that should detect the interaction with a protein; for example, the loop portion of RNA having a stem-loop structure, more specifically, RNA having 500 bases or less, 400 bases or less, 300 bases or less, 200 bases or less, 150 bases or less, 100 bases or less or 50 bases or less. Preferable RNA is a loop portion contained in any Pre-miRNA.

In the present invention, Pre-miRNA refers to a single stranded RNA containing miRNA and its complementary strand and is capable of forming a hairpin loop structure. In the present invention, miRNA refers to a short-chain (20-25 base) non-coding RNA present in a cell and involved in regulation of gene expression by inhibiting translation from mRNA to a protein and decomposing mRNA. The miRNA is transcribed as Pri-miRNA, partially cleaved by an enzyme called Drosha present in the nucleus into Pre-miRNA, transported outside the nucleus, further cleaved by Dicer into a no-stem structure, and then serves as a single stranded RNA (mature miRNA). Accordingly, in the present invention, the loop region contained in Pre-miRNA is indistinguishable from the loop region contained in Pri-miRNA. The sequence of Pre-miRNA can be available from the information of the database (for example, http://www.mirbase.org/ or http://www.microRNA.org/) as a stem-loop sequence. The preferable Pre-miRNA sequence in the present invention is that derived from a human or mouse.

In the present invention, the loop portion contained in a Pre-miRNA refers to a single stranded RNA portion of the Pre-miRNA, having a sequence except a part of mature miRNA and its complementary strand, for example, can be extracted by the method defined as follows.

(I) Case in Which Pre-miRNA Contains a Single Mature miRNA (1) When mature miRNA is present on the 5' side of the loop, the loop portion contained in Pre-miRNA starts from the 4th base (the start point) from the 3' end of the mature miRNA and ends at a base (the end point) making a pair with the base of the start point (see FIG. 1A, lower stage). At this time, when the base to be paired with is not present due to mismatch, the base making a pair with the next (second) base to the start point on the 3' side is specified, as the end point.

(2) When mature miRNA is present on the 3' side of the loop, the loop portion contained in Pre-miRNA ends at the 4th base (the end point) from the 5' end of the mature miRNA and starts at the base (the start point) making a pair with the base at the start point (see FIG. 1A, upper stage). At this time, when the base to be paired with is not present due to mismatch, the base making a pair with the next (second) base to the end point on the 5' side is specified as the start point.

(II) Case in Which Pre-miRNA Contains Two or More Mature miRNAs (1) When mature miRNA, which is positioned farther from the loop side, is present on the 5' side of the loop, the loop portion contained Pre-miRNA starts from the 4th base (the start point) from the 3' end of the mature miRNA and ends at a base (the end point) making a pair with the base of the start point. At this time, when to base to be paired with is not present due to mismatch, the base making a pair with the next (second) base of the start point on the 3' side is specified as the end point.

(2) When mature miRNA, which is positioned farther from the loop side, is present on the 3' side of the loop, the loop portion contained in Pre-miRNA ends at the 4th base (the end point) from the 5' end of the mature miRNA and starts at the base (the start point) making a pair with the base at the start point. At this time, when the base to be paired with is not present due to mismatch, the base making a pair with the next (second) base of the end point on the 5' side is specified as the start point.

The present invention provides a method for producing an RNA microarray, including a step of hybridizing RNA probes mentioned above with an immobilization support such as microbeads or a glass slide, to which DNA barcode sequences are attached. In the present invention, examples of the immobilization support include semiconductors such as silicon, inorganic materials such as glass and diamond and films mainly made of a polymer substance such as polyethylene terephthalate and polypropylene. Examples of the form of a substrate include, but are not limited to, a glass slide, a microwell plate, microbeads and fibrous forms.

Examples of a method for attaching a DNA barcode sequence onto the immobilization support include, but are not limited to, a method involving attaching a functional group such as an amino group, an aldehyde group, an SH group and biotin in advance to a nucleic acid having a DNA barcode sequence, and attaching a functional group (e.g., an aldehyde group, an amino group and an SH group, streptavidine) capable of reacting with the nucleic acid also into, an immobilization support, and crosslinking the immobilization support and the nucleic acid via a covalent bond between functional groups; and a method of coating an immobilization support with a polycation and electrostatically immobilizing a polyanionic nucleic acid to the immobilization support. Examples of a method for preparing a DNA barcode sequence include an Affymetrix system, in which a nucleic acid probe is synthesized by connecting nucleotides one by one on a substrate (e.g., glass, silicon) by use of photolithography; and a Stanford system, in which a nucleic acid having DNA barcode sequence previously prepared is spotted onto a substrate, by use of e.g., a micro-spotting method, an ink-jet method or a bubble jet (registered trademark) method. When a probe of 30-mer or more is used, the Stanford system or a combination of both methods is preferably used. The immobilization support having a DNA barcode sequence attached thereon can be prepared by an outsourcer.

The immobilization support having a DNA barcode sequence attached thereto prepared as mentioned above can be hybridized with a RNA probe to specifically bind the immobilization support and the RNA probe. One skilled in the an can perform hybridization by appropriately changing the salt concentration, of a hybridization solution, temperature, probe concentration, reaction time, the salt concentration of a washing liquid, the temperature of the washing process and the like.

One hundred or more RNA probes can be spotted on the same immobilization support (for example, 1-inch×3-inch glass slide) by using the method of the present invention. An RNA microarray having RNA probes at the same density as in a DNA microarray, for example, 500 or more, 1,000 or more, 2,000 or more, 3,000 or more, 4,000 or more, 5,000 or more and 10,000 or more, can be provided.

In the present invention, a protein in a solvent is supplied to the RNA microarray having RNA probes. In this manner, an RNA probe interacting with the protein can be detected. As the solvent used herein, an aqueous solution containing, for example, Tris-HCl 20 mM, NaCl 300 mM, 5 mM $MgCl_2$ and 0.1% Tween-20, may be mentioned. The protein may be labeled with a radioactive isotope, digoxigenin (DIG), a fluorescent dye (for example, FITC, PE, Cy3 and Cy5) and the like for detection and preferably tagged with a different label from that attached to the RNA probe. More preferably, the RNA probe is labeled with Cy5 and the protein is labeled with Cy3. In the present invention the interaction means binding of a protein and an RNA probe. The "binding" herein refers to a state for functionally binding two molecules (called "physical binding") known in the art. Examples of the physical binding include, but are not limited to, non-covalent bindings, covalent bindings (for example, disulfide bond and covalent bond), hydrogen binding, electrostatic binding and conformation binding (for example, key-keyhole binding). In other words, the interaction refers to the case in which if a protein is supplied to the RNA microarray in the present invention and thereafter the microarray is washed with the solvent mentioned above, the protein still remains bound.

In the present invention, a first method for detecting interaction between a protein and an RNA probe is characterized by comprising the following steps;
1) a step of bringing an RNA microarray containing RNA probes into contact with the protein,
2) a step of measuring the interaction between the RNA probe and the protein in step 1 by a measuring means based on a labeling substance to the protein, and
3) a step of calculating the amount of protein on the RNA microarray based on the measurement results obtained in step 2.

As the measuring means, an analytical instrument having a function of detecting the presence of the labeling substance and quantifying the amount thereof is used. If the labeling substance is a fluorescent substance, an instrument having an optical detection apparatus is used.

The "calculating" is calculating the amount of protein in the RNA probe by using the amount of labeling substance tagged to the protein attached to the RNA probe, which was previously confirmed not to interact with the protein for use in detection.

In the present invention, if an RNA probe provides a higher value than the amount of labeling substance tagged to the protein attached to the RNA probe previously confirmed not to interact with the protein, the protein is detected as the one interacting with the RNA probe providing the higher value.

In the present invention, in order to prevent false-positives in detecting the interaction between a protein and an RNA probe, the RNA microarray preferably contains RNA probes of two or more types, which are identical in sequences (ii), (iii) and (iv) (collectively referred to as a protein recognition site):
(ii) the sequence of the first stem portion,
(iii) the sequence of the second stem portion complementary to the first stem portion, for hybridizing with the first stem portion to form a double-stranded stem, and
(iv) the sequence of a loop portion contained in Pre-miRNA and linking the two stem portions;
and which differ in
(i) complementary strand sequence to the DNA barcode sequence.

When a target protein was supplied to the RNA microarray containing RNA probes of two or more types having the same protein recognition site and a different complementary strand sequence (i) to DNA barcode sequence and if it can be detected that the RNA probe having the same protein recognition site interacts with the target protein in a rate of 20% or more, 25% or more, 33% or more, 50% or more, 66% or more, 75% or more or 100%, it can be said that the protein recognition site interacts with the target protein.

The interaction with RNA probes having protein recognition sites of 35 bases or more can be simultaneously detected by using the method of the present invention. The present invention can be applied to an RNA probe having, for example, protein recognition sites of 40 bases or more, 50 bases or more, 60 bases or more, or 70 bases or more.

In the present invention, it was confirmed that a protein interacts with a DNA barcode sequence. Because of this, in order to specifically detect a protein interacting only with the protein recognition site of an RNA probe in the first method, the following second method can be used:

1) a step of bringing an RNA microarray containing an RNA probe into contact with a sample containing the target protein, 2) a step of bringing a DNA microarray, which contains a DNA barcode sequence and does not contain the RNA probe, into contact with the sample containing target protein, 3) a step of measuring the interaction between the RNA probe and the protein in step 1 by a measuring means based on a labeling substance to the protein, 4) a step of calculating the amount of protein on the RNA microarray based on the measurement results obtained in step 3, 5) a step of measuring the interaction between a DNA barcode sequence and the protein in step 2 by the measuring means based on a labeling substance to the protein, 6) a step of extracting the corresponding DNA barcode sequence based on the measurement results obtained in step 5, and 7) a step of eliminating the RNA probe corresponding to the DNA barcode sequence extracted in step 6 from the RNA probes which are detected as those interacting with the target protein by the calculation in step 4.

More specifically, the second method is the one containing the following steps:

(1) a step of bringing an RNA microarray containing RNA probes and a slide having a DNA barcode sequence attached thereto and no RNA probe hybridized therewith, into contact with a fluorescence-labeled target protein, (2) a step of identifying an RNA probe and DNA barcode sequence, which were bound to the target protein, and (3) a step of obtaining an RNA probe by eliminating the RNA probe having a complementary strand corresponding to the DNA barcode sequence and identified in step (2) from the RNA probes identified in step (2), and detecting Pre-miRNA containing a sequence contained in the RNA probe obtained, as the Pre-miRNA which binds to the target protein.

In the present invention, noise produced by the interaction between the target protein and the DNA barcode sequence is eliminated and an RNA probe specifically interacting with the target protein can be detected by using the second method.

In the first method and second method of the present invention, detection can be made at a concentration of the target protein (to be subjected to the microarray) of 5 nM, 10 nM, 20 nM, 30 nM, 40 nM, 50 nM, 60 nM, 70 nM, 80 nM, 90 nM, or 100 nM; and more preferably, 40 nM or less.

In the present invention, a third method for detecting the interaction between a protein and an RNA probe, is characterized by comprising the following steps:

(1) a step of bringing the RNA probe into contact with a target protein, (2) a step of isolating the target protein obtained in step (1) while maintaining binding to the RNA probe, (3) a step of extracting the RNA probe from the target protein obtained in step (2), (4) a step of bringing the RNA probe obtained in step (3) into contact with a slide having a DNA barcode sequence attached thereto, (5) a step of identifying the RNA probe hybridized with the slide having the DNA barcode sequence attached thereto, and (6) a step of detecting RNA containing the sequence (iv) contained in the RNA, probe identified in step (5) as the RNA which binds to the target protein.

In the third method of the present invention, in order to isolate a target protein while maintaining the binding with the RNA probe in step (2), the target protein may be bound to a carrier such as a resin. In the present invention, the carrier may be magnetic beads. In order to bind to a target protein, the carrier is preferably crosslinked or, coated with protein A, G, or L, a metal ion (for example, copper, nickel, zinc, cobalt ions), biotin or glutathione. The target protein may have a tag such as a His tag or a GST tag in order to bind, to e.g., a carrier. Alternatively, an antibody specific to the target protein may be used.

The RNA probe to be used in the third method of the present invention may be used in an amount, of 100 μg or less and more preferably 1 μg.

In step (5) of the third method of the present invention, the fluorescent dye label of an RNA probe is detected; DNA barcode sequence corresponding to the position of the slide at which the fluorescent dye is detected is identified and then RNA probe having the DNA barcode sequence is searched. In this way, the RNA probe can be identified.

In the third method of the present invention, detection can be made at a concentration of the target protein (to be supplied to a microarray) of 100 pM or less, for example, 1 pM, 2 pM, 3 pM 4 pM, 5 pM, 10 pM, 20 pM, 30 pM, 40 pM, 50 pM, 60 pM, 70 pM, 80 pM, 90 pM, or 100 pM, and more preferably 20 pM or less.

Now, typical Examples of the present invention will be described referring to the drawings attached to the present application; however, the technical scope of the present invention is not limited to these specific embodiments.

Example 1

1. PCR Amplification of Template DNA

The template DNA sequence of an RNA probe was designed so as to have (i) Adjuster Sequence. (ii) CC+T7 promoter+G (24 bases), (iii) Complementary sequence of 25-mer DNA Barcode (25 bases), (iv) G+Stem forward sequence (18 bases), (v) Designed RNA coding Sequence and (vi) Stem reverse Sequence (17 bases) sequentially from the 5' end (FIG. 1A). The individual sequences were as follows:

(i) Adjuster Sequence

OLIGONUCLEOTIDE LIBRARY SYNTHESIS (OLS) (Agilent Technologies) was used. To synthesize a template DNA, setting the total length to be 180 bases, the length of the Adjuster Sequence was defined by the number of bases, which was obtained by subtracting the number of bases of Designed RNA coding Sequence from 96 bases. As the sequence, a requisite number of bases from the 5' end of 5'-CAGAGCTCTCTGGCTAACTAGAGAACC-CACTGCTTACTGGCTTATACCAAAATCA ACGGGACTTTCCAAAATAGTTATTAATAGTAAT-3' (SEQ ID No. 1), was used.

(ii) CC+T7 Promoter+G (24 Bases)

(SEQ ID. No. 2)
5'-CCGCGCTAATACGACTCACTATAG-3'

(iii) Complementary Sequence of 25-mer DNA Barcode (25 Bases)

Complementary strands to bc25mer_1 to bc25mer_6500 of 240000 types of 25-base length DNA sequences (bc25mer_1-240000) disclosed in Xu, Q., Schlabach, M. R., Hannon, G. J. et al. (2009) PNAS 106, 2289-2294, were used.

(iv) G+Stem Forward Sequence (18 Bases)

5'-GGTGTACGAAGTTTCAGC-3' (SEQ ID No. 3)

(v) Designed RNA Coding Sequence

From the sequences (Pre-miRNA sequence) corresponding to Accession Numbers of human 1872 types and mouse 1186 types disclosed in miRBase release 20 (http://www.mirbase.org/), the sequences of a Stem-loop structure and mature miRNA were obtained and the Designed RNA coding Sequences (loop regions) wore defined as follows and extracted. Herein, the loop regions of four Pre-miRNAs, i.e., hsa-mir-3652 (MI0022909), hsa-mir-6753 (MI0016052), hsa-mir-6892 (MI0022598) and mmu-mir-7060 (MI10022739), have chain lengths longer than 96 bases and exceed the chain length (180 bases) of the template DNA sequence, and thus, these four loops were removed from a library. Accordingly, the library was prepared from the loop regions of human 1869 types and mouse 1185 types.

(1) The loop region of Pre-miRNA starts from the 5' end side and terminated at the 3' end side.

(2) Regardless of formation of a base pair, the start point and end point of Designed RNA coding Sequence are defined as bases in the same row in the figure of the Stem-loop secondary structure estimated by the miRBase.

Figure 2B:
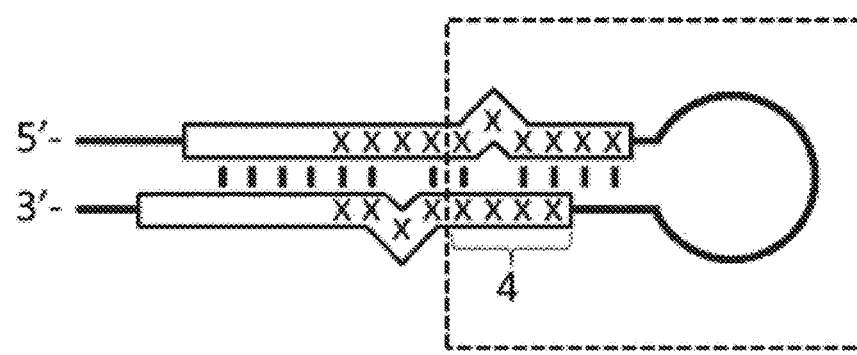

(3) When Pre-miRNA contains a single mature miRNA sequence (FIG. 2A), the loop region (dotted-line Box) starts at the 4th base of the mature miRNA (solid-line Box) and ends at the base at the same position in the lower column. When Pre-miRNA contains two mature miRNA sequences (FIG. 2B), the sequence of mature miRNA, the loop region side of which is further from the loop region is selected and the row of the 4th base from the loop region side of the selected mature miRNA is defined as the start point and the end point positions of the loop region (dotted-line Box).

(vi) Stem reverse sequence (17 bases)

5'-GCTGAAGCTTCGTGCAC-3' (SEQ ID No. 4)

We outsourced to Agilent Technologies to synthesize the template DNA sequence thus designed by using a complementary strand as a single stranded DNA and OLIGONUCLEOTIDE LIBRARY SYNTHESIS (FIG. 1B). Using the single stranded DNA as a template, Forward primer (5'-CCGCGCTAANTACGACTCACTATAGG-3' (SEQ ID No. 5)) and Reverse primer (5'-GTGCACGAAGCTTCAGC-3' (SEQ ID No. 6)), a template DNA double stranded (Template dsDNA) was amplified by PCR.

Note that, in the present invention, an RNA probe was designated in accordance with the following rule: "xxxxx" of RNP_xxxxx denotes the number of 25 mer barcode DNA.

The loop regions of 1869 types of human Pre-miRNAs were prepared so as to have two or three different types of Complementary sequences of 25-mer DNA Barcode relative to the same loop region as described below:

first human Pre-miRNA loop library: from RNP_0008 to RNP_00028 and RNP_00030-RNP_01887, second human Pre-miRNA loop library: RNP_01888-RNP_03756, and third human Pre-miRNA loop library: RNP_03757-RNP_05315.

For reference, sequences of RNP_00001 to RNP_00029 are shown in Table 1.

TABLE 1A

| RNA probe ID | Name of loop sequence | Template ssDNA sequence | SEQ. ID No. |
|---|---|---|---|
| RNP_00001 | Kt | GTGCACGTAGCTTCAGCATCACGCCCTTTCGGGTCAGCTGAAACTTCGTACACCTATGAGGACGAATCTCCCGCTTATACTATAGTGAGTCGTATTAGCGCGGTAACTATTTTGGAAAGTCCCGTTGATTTTGGTATAAGCCAGTAAGCAGTGGGTTCTCTAGTTAGCCAGAGAGCTCTG | 7 |
| RNP_00002 | 1xKloop | GTGCACGAAGCTTCAGCGGGTGATCACCGTTCACACCCGCTGAAACTTCGTACACCGGTCTTGACAAACGTGTGCTTGTACCTATAGTGAGTCGTATTAGGGCGGACTATTTTGGAAAGTCCCGTTGATTTTGGTATAAGCCAGTAAGCAGTGGGTTCTCTAGTTAGCCAGAGAGCTCTG | 8 |
| RNP_00003 | 2xKloop | GTGCACGAAGCTTCAGCGGGTGATCACCGTTCACACCCGGATCTCGGGTGATCACCGTTCACACCCGCTGAAACTTCGTACACCGTTTATCGGGCGTGGTGCTCGCATACTATAGTGAGTCGTATTAGCGCGGGTATAAGCCAGTAAGCAGTGGGTTCTCTAGTTAGCCAGAGAGCTCTG | 9 |
| RNP_00004 | 3xKloop | GTGCACGAAGCTTCAGCGGGTGATCACCGTTCACACCCGGATCTCGGGTGATCACCGTTCACACCCGGATCTCGGGTGATCACCGTTCACACCCGCTGAAACTTCGTACACCCCGATGTTGACGGACTAATCCTGACCTATAGTGAGTCGTATTAGCGCGGAGTTAGCCAGAGAGCTCTG | 10 |
| RNP_00005 | 2xMS2SL | GTGCACGAAGCTTCAGCCGATGGGTGATCCTCACCGGATCTCGATGGGTGATCCTCACCGCTGAAACTTCGTACACCTAGTAGTTCAGACGCCGTTAAGCGCCTATAGTGAGTCGTATTAGCGCGGGATTTTGGTATAAGCCAGTAACCAGTGGGTTCTCTAGTTAGCCAGAGAGCTCTG | 11 |

TABLE 1A-continued

| RNA probe ID | Name of loop sequence | Template ssDNA sequence | SEQ. ID No. |
|---|---|---|---|
| RNP_00006 | CLIP34nt_UG6 | GTGCACGAAGCTTCAGCTTATGCACCACCACACACACAC GCGCTCTCTCGCTGAAACTTCGTACACCCCGTACCTAGATAC ACTCAATTTGTCTATACTGAGTCCTATTAGCGCGGGTCCCGT TGATTTTGGTATAAGCCAGTAAGCAGTGGGTTCTCTAGTTAG CCAGAGAGCTCTG | 12 |

TABLE 1B

| RNA probe ID | Name of loop sequence | Template ssDNA sequence | SEQ. ID No. |
|---|---|---|---|
| RNP_00007 | UG12 | GTGCACGAAGCTTCAGCACACACACACACACACACACAC AGCTGAAACTTCGTACACCGGSGTTCCGTTTTACATTCCAGG AACTATAGTGAGTCGTATTAGCGCGGTTTTGGAAAGTCCCGT TGATTTTGGTATAAGCCAGTAAGCAGTGGGTTCTCTAGTTAG CCAGAGAGCTCTG | 13 |
| RNP_00008 | dKt | GTGCACGAAGGTTCAGCATGACGCCCTTTCGGGCAGCTGAA ACTTCGTACACCTATCCCGTGAAGCTTGAGTGGAATCCTATA GTGAGTCGTATTAGCGCGGATAACTATTTTGGAAAGTCCCGT TGATTTTGGTATAAGCCAGTAAGCAGTGGGTTCTCTAGTTAG CCAGAGAGGTCTG | 14 |
| RNP_00009 | U1A2 | GTGCACGAAGCTTCAGCGGTGCAATGTCCCGAAGGACTCGC TGAAACTTCGTACACCCTGACGTGTGAGGCGCTAGAGCATA CTATAGTGAGTCGTATTAGCGCGGCTATTTTGGAAAGTCCCG TTGATTTTGGTATAAGCCAGTAAGCAGTGGGTTCTCTAGTTA GCCAGAGAGCTCTG | 15 |
| RNP_00010 | U1A2 | GTGCACGAAGCTTCAGCGGTGCAATGTCCCGAAGGACTCGC TGAAACTTCGTACACCGGTATGGCACGCCTAATCTGGACACC TATAGTGAGTCGTATTAGCGCGGCTATTTTGGAAAGTCCCGT TGATTTTGGTATAAGCCAGTAAGCAGTGGGTTCTCTAGTTAG CCAGAGAGCTCTG | 16 |
| RNP_00011 | dU1A2 | GTGCACGAAGCTTCAGCGCCGTAATGTCCCGAAGGACTCGC TGAAACTTCGTACACCGGATGCATGATCTAGGGGCTCGTCTC TATAGTGAGTCGTATTAGCGCGGCTATTTTGGAAAGTCCCGT TGATTTTGGTATAAGCCAGTAAGCAGTGGGTTCTCTAGTTAG CCAGAGAGCTCTG | 17 |
| RNP_00012 | dU1A2 | GTGCACGAAGCTTCAGCGCCGTAATGTCCCGAAGGACTCGC TGAAACTTCGTACACCGAGGTCTTTCATGCGTATAGTCACAC TATAGTGAGTCGTATTAGCGCGGCTATTTTGGAAAGTCCCGT TGATTTTGGTATAAGCCAGTAAGCAGTGGGTTCTCTAGTTAG CCAGAGAGCTCTG | 18 |

TABLE 1C

| RNA probe ID | Name of loop sequence | Template ssDNA sequence | SEQ. ID No. |
|---|---|---|---|
| RNP_00013 | U1A | GTGCACGAAGCTTCAGCGGAGTGCAATGCTGAAACTTCGTA CACCGATTCAATATGTGTCGTCTATCCTCCTATAGTGAGTCG TATTAGCGCGGTACTATTAATAACTATTTTGGAAAGTCCCGTT GATTTTGGTATAAGCCAGTAAGCAGTGGGTTCTCTAGTTAGC CAGAGAGCTCTG | 19 |
| RNP_00014 | U1A | GTGCACGAAGCTTCAGCGGAGTGCAATGCTGAAACTTCGTA CACCGGTAACTGCGCATAGTTGGCTCTATCTATAGTGAGTCG TATTAGCGCGGTACTATTAATAACTATTTTGGAAAGTCCCGTT GATTTTGGTATAAGCCAGTAAGCAGTGGGTTCTCTAGTTAGC CAGAGAGCTCTG | 20 |

TABLE 1C-continued

| RNA probe ID | Name of loop sequence | Template ssDNA sequence | SEQ. ID No. |
|---|---|---|---|
| RNP_00015 | dU1A | GTGCACGAAGCTTCAGCGGACCGTAATGCTGAAACTTCGTACACCGCGTTTAAGGTCACATCGCATGAATCTATAGTGAGTCTGTATTAGCGCGGTACTATTAATAACTATTTTGGAAAGTCCCGTTGATTTTGGTATAAGCCAGTAAGCAGTGGGTTCTCTAGTTAGCCAGAGAGCTCTG | 21 |
| RNP_00016 | dU1A | GTGCACGAAGCTTCAGCGGACCGTAATGCTGAAACTTCGTACACCGCCCGGGAAGTGTGAGGATATACCCCTATAGTGAGTCGTATTAGCGCGGTACTATTAATAACTATTTTGGAAAGTCCCGTTGATTTTGGTATAAGCCAGTAAGCAGTGGGTTCTCTAGTTAGCCAGAGAGCTCTG | 22 |
| RNP_00017 | MRPL9 3'UTR IGF2BP | GTGCACGAAGCTTCAGCTGGGATACAAATGTTCAGTTTGGATGATGAGAATGAGGCAAGTAGTGGAGACAGCTGAAACTTCGTACACCGCTCTTAAAACTGGTATCACCTGACCTATAGTGAGTCGTATTAGCGCGAAGCCAGTAAGCAGTGGGTTCTCTAGTTAGCCAGAGAGCTCTG | 23 |
| RNP_00018 | hsa-let-7a-1 | GTGCACGAAGCTTCAGCATAGTTATCTCCCAGTGGTGGGTGTGACCCTAAAACTATGCTGAAACTTCGTACACCGGGTGGTTAGTGATTTGCCCGTCACCTATAGTGAGTCGTATTAGCGCGGGTTGATTTTGGTATAAGCCAGTAAGCAGTGGGTTCTCTAGTTAGCCAGAGAGCTCTG | 24 |

TABLE 1D

| RNA probe ID | Name of loop sequence | Template ssDNA sequence | SEQ. ID No. |
|---|---|---|---|
| RNP_00019 | hsa-let-7a-2 | GTGCACGAAGCTTCAGCACAGTTATCTCCCTTGATGTAATTCTAAACTATGCTGAAACTTCGTACACCTAGTTGGTGGGTTTCCCTACCGTGTCTATAGTGAGTCGTATTAGCGCGGAGTCCCGTTGATTTTGGTATAAGCCAGTAAGCAGTGGGTTCTCTAGTTAGCCAGAGAGCTCTG | 25 |
| RNP_00020 | hsa-let-7a-3 | GTGCACGAAGCTTCAGCATAGTTATCCCATAGCAGGGCAGAGCCCCAAACTATGCTGAAACTTCGTACACCGGTACAGTAAGTGAGAATCCTCTCTATAGTGAGTCGTATTAGCGCGGCCCGTTGATTTTGGTATAAGCCAGTAAGCAGTGGGTTCTCTAGTTAGCCAGAGAGCTCTG | 26 |
| RNP_00021 | hsa-let-7b | GTGCACGAAGCTTCAGCATAGTTATCTTCCGAGGGGCAACATCACTGCCCTGAAACCACGCTGAAACTTCGTACACCGGTTCTAAGTTTAGCGTAGCCGGTTCTATAGTGAGTCGTATTAGCGCGGGATTTTGGTATAAGCCAGTAAGCAGTGGGTTCTCTAGTTAGCCAGAGAGCTCTG | 27 |
| RNP_00022 | hsa-let-7c | GTGCACGAAGCTTCAGCAGTTAACTCCCAGGGTGTAACTCTAAACCGCTGAAACTTCGTACACCCTTTAGGTGGGTGCGATTGCCAGTTCTATAGTGAGTCGTATTAGCGCGGGGAAAGTCCCGTTGATTTTGGTATAAGCCAGTAAGCAGTGGGTTCTCTAGTTAGCCAGAGAGCTCTG | 28 |
| RNP_00023 | hsa-let-7d | GTGCACGAAGCTTCAGCATAGTTACCTCCTTGTGGGCAAAATCCCTGCCCTAAAACTATGCTGAAACTTCGTACACCGCCACCTTAACACGCGATGATATTGCTATAGTGAGTCGTATTAGCGCGGGATTTTGGTATAAGCCAGTAAGCAGTGGGTTCTCTAGTTAGCCAGAGAGCTCTG | 29 |
| RNP_00024 | hsa-let-7e | GTGCACGAAGCTTCAGCATAGTGATCTCCTTGGGTGTCCTCTCAACTATGCTGAAACTTCGTACACCGCTATTACGAGCGCTTGGATCCCGTCTATAGTGAGTCGTATTAGCGCGGAGTCCCGTTGATTTTGGTATAAGCCAGTAAGCAGTGGGTTCTCTAGTTAGCCAGAGAGCTCTG | 30 |

TABLE E1

| RNA probe ID | Name of loop sequence | Template ssDNA sequence | SEQ. ID No. |
|---|---|---|---|
| RNP_00025 | hsa-let-7f-1 | GTGCACGAAGCTTCAGCATAGTTATCTCCTGAACAGGGTAAA ATCACTACCCCACAACTATGCTGAAACTTCGTACACCTATGTT GTGCCTTACGCCTCGATTACTATAGTGAGTCGTATTAGCGCG GTTTTGGTATAAGCCAGTAAGCAGTGGGTTCTCTAGTTAGCC AGAGAGCTCTG | 31 |
| RNP_00026 | hsa-let-7f-2 | GTGCACGAAGCTTCAGCATAGTTATCTCCAAGATGGGGTATG ACCCTAAAACTATGCTGAAACTTCGTACACCTTAACCGAACT GACGGCCATCAAGGCTATAGTGAGTCGTATTAGCGCGGCGT TGATTTTGGTATAAGCCAGTAAGCAGTGGGTTCTCTAGTTAG CCAGAGAGCTCTG | 32 |
| RNP_00027 | hsa-let-7g | GTGCACGAAGCTTCAGCACAGTTATCTCCTGTACCGGGTGG TATCATAGACCCTCAAACTGTGCTGAAACTTCGTACACCGGG TACATGCGCCTTACTCCTTGTGCTATAGTGAGTCGTATTAGC GCGGTTTGGTATAAGCCAGTAAGCAGTGGGTTCTCTAGTTAG CCAGAGAGCTCTG | 33 |
| RNP_00028 | hsa-let-7i | GTGCACGAAGCTTCAGCGCAGTTATCTCCACAGCGGGCAAT GTCACAACCCGACCAACAGCGCTGAAACTTCGTACACCTTCT ATTCTAAGCCGGCGGTCATATCTATAGTGAGTCGTATTAGCG CGGTTTTGGTATAAGCCAGTAAGCAGTGGGTTCTCTAGTTAG CCAGAGAGCTCTG | 34 |
| RNP_00029 | let7 consensus | GTGCACGAAGCTTCAGCGGGCTCCTTGCCCGCTGAAACTTC GTACACCGCTTGATGCTTTACAAGATCGCGTTCTATAGTGAG TCGTATTAGCGCGGTATTAATAACTATTTTGGAAAGTCCCGTT GATTTTGGTATAAGCCAGTAAGCAGTGGGTTCTCTAGTTAGC CAGAGAGCTCTG | 35 |

2. Synthesis of RNA Probe by In-Vitro Transcription from Double Stranded DNA

An RNA probe was transcribed from the obtained Template dsDNA using the in-vitro transcription system (MEGAshortscript™ T7 Transcription Kit, Life Technologies) in accordance with the manufacturer's protocol (FIG. 1C).

3. Cy5 Fluorescence Label of RNA Probe

The 3' end of the obtained RNA probe was modified by adding pCp-Cy5 by use of T4 RNA ligase.

4. Hybridization of RNA Probe with the DNA Barcode on Microarray

Of the 240,000 types of 25-base length DNA sequences (bc25mer_1-240000) disclosed in Xu, Q., Schlabach, M. R., Hannon, G. J. et al. (2009) PNAS 106, 2289-2294, DNA sequences from bc25mer_10667 were spotted on a slide. The slide was prepared by an outsourcer, Agilent Technologies. To the slide, the RNA probes were added to perform hybridization in accordance with the slide manufacturer's protocol (8×15 K, 8×60 K Agilent Oligo microarray Protocol).

5. Binding with Fluorescence-Labeled Protein

Cy3 fluorescence-labeled NHS (N-Hydroxysuccinimide) ester was reacted with a target protein to prepare a Cy3-labeled target protein. The protein was diluted with an appropriate buffer and added to the microarray slide obtained in Section 4 and washed. In this manner, the protein was allowed to specifically bind to the RNA probes.

6. 2-Color Scan Method (Cy3/Cy5) of Microarray Slide

The fluorescence intensity of Cy3 and Cy5 was measured by using a microarray scanner. From individual fluorescence intensity values, the presence or absence of RNA-protein interaction and the strength of the interaction were roughly calculated.

Example 2

Confirmation of Interaction Between L7Ae or U1A Protein and RNA Probe

1. Design of Template DNA Sequence

Using Kt sequence binding to ribosomal protein L7Ae (AAB90466) of Archaebacteria, a binding mutant sequence dKt, 2 types of sequences, U1A and U1A2, binding to human U1A protein (NP_004587), and respective binding mutant sequences thereof, dU1A and dU1A2, loop sequences of hsa-Pre-let7 family (hsa-Pre-let7 a-1 (miRBase Accession No: MI0000060), a-2 (miRBase Accession No: MI0000061), a-3 (miRBase Accession No: MI0000062), b (miRBase Accession No: MI0000063), c (miRBase Accession No: MI0000064), d (miRBase Accession No: MI0000065), e (miRBase Accession No: MI0000066), f-1 (miRBase Accession No: MI0000067), f-2 (miRBase Accession No: MI0000068), g (miRBase Accession No: MI0000433), i (miRBase Accession No: MI0000434)), which were obtained by the method of Example 1 from the miRBase, and le7 family consensus sequences, as Designed RNA coding Sequence, Template DNA sequences (Table 2) were designed. Note that, in this example, the Adjuster Sequence was added only to template DNA sequences for hsa-Pre-let7 family and le7 consensus sequence so as to obtain a full length of 130 bases.

TABLE 2A

| RNA probe name | Template ssDNA sequence (Complementary strand of template DNA sequence) | SEQ. ID No. |
|---|---|---|
| PoP_00001_Kt | 5'-GTGCACGAAGCTTCAGCATCACGCCCTTTCGGGTCAGCTGAAACTTCGTACACCTATGAGGACGAATCTCCCGCTTATACTATAGTGAGTCGTATTAGCGCGG-3' | 36 |
| PoP_00008_dKt | 5'-TCCGGGAATATAGCGCCATGACGCCCTTTCGGGCAGGCACTATATTCCCAAACTATCCCGTGAAGCTTGAGTGGAATCCTATAGTGAGTCGTATTAGCGCGG-3' | 37 |
| PoP_00010_U1A2 | 5'-TCCGGGAATATAGCGCCGGTGCAATGTCCCGAAGGACTCGGCACTATATTCCCAAACGGTATGGCACGCCTAATCTGGACACCTATAGTGAGTCGTATTAGCGCGG-3' | 38 |
| PoP_00011_dU1A2 | 5'-TCCGGGAATATAGCGCCGCCGTAATGTCCCGAAGGACTCGGCACTATATTCCCAAACGGATGCATGATCTAGGGCCTCGTCTCTATAGTGAGTCGTATTAGCGCGG-3' | 39 |
| PoP_00014_U1A | 5'-TCCGGGAATATAGCGCCGGAGTGCAATGGCACTATATTCCCAAACGGTAACTGCGCATAGTTGGCTCTATCTATAGTGAGTCGTATTAGCGCGG-3' | 40 |
| Pop_00016_dU1A | 5'-TCCGGGAATATAGCGCCGGACCGTAATGGCACTATATTCCCAAACGCCCGGGAAGTGTGAGGATATACCCCTATAGTGAGTCGTATTAGCGCGG-3' | 41 |
| PoP_00018_hsa-let-7a-1 | 5'-GTGCACGAAGCTTGAGCATAGTTATCTCCCAGTGGTGGGTGTGACCCTAAAACTATGCTGAAACTTCGTACACCGGGTGGTTAGTGATTTGCCCGTCACCTATAGTGAGTCGTATTAGCGCGGAGCTCTG-3' | 42 |
| PoP_00019_hsa-let-7a-2 | 5'-GTGCACGAAGCTTCAGCACAGTTATCTCCCTTGATGTAATCTAAACTATGCTGAAACTTCGTACACCTAGTTGGTGGGTTTCCCTACCGTGTCAGTGAGTCGTATTAGCGCGGCCAGAGAGCTCTG-3' | 43 |
| PoP_00020_hsa-let-7a-3 | 5'-GTGCACGAAGCTTCAGCATAGTTATCCCATAGCAGGGCAGAGCCCCAAACTATGCTGAAACTTCGTACACCGGTACAGTAAGTGAGAATCCTCTCTCTATAGTGAGTCGTATTAGCGCGGGAGAGCTCTG-3' | 44 |
| PoP_00021_hsa-let-7b | 5'-GTGCACGAAGCTTCAGCATAGTTATCTTCCGAGGGGCAACATCACTGCCCTGAAACCACGCTGAAACTTCGTACACCGGTTCTAAGTTTAGCGTAGCCGGTTCTATAGTGAGTCGTATTAGCGCGGTCTG-3' | 45 |

TABLE 2B

| RNA probe name | Template ssDNA sequence (Complementary strand of template DNA sequence) | SEQ. ID No. |
|---|---|---|
| PoP-00022_hsa-let-7c | 5'-GTGCACGAAGCTTCAGCAGTTAACTCCCAGGGTGTAACTCTAAACCGCTGAAACTTCGTACACCCTTTAGGTGGGTGCGATTGCCAGTTCTATAGTGAGTCGTATTAGCGCGGTTAGCCAGAGAGCTCTG-3' | 46 |
| PoP_00023_hsa-let-7d | 5'-GTGCACGAAGCTTCAGCATAGTTACCTCCTTGTGGGCAAAATCCCTGCCCTAAAACTATGCTGAAACTTCGTACACCGCCACCTTAACACGCGATGATATTGCTATAGTGAGTCGTATTAGCGCGGTCTG-3' | 47 |
| PoP_00024_hsa-let7e | 5'-GTGCACGAAGCTTCAGCATAGTGATCTCCTTGGGTGTCCTCCTCAACTATGCTGAAACTTCGTACACCGCTATTACGAGCGCTTGGATCCCGTCTATAGTGAGTCGTATTAGCGCGGCCAGAGAGCTCTG-3' | 48 |
| PoP_00025_hsa-let-7f-1 | 5'-GTGCACGAAGCTTCAGCATAGTTATCTCCTGAACAGGGTAAAATCACTACCCCACAACTATGCTGAAACTTCGTACACCTATGTTGTGCCTTACGCCTCGATTACTATAGTGAGTCGTATTAGCGCGGTCTG-3' | 49 |

TABLE 2B-continued

| RNA probe name | Template ssDNA sequence (Complementary strand of template DNA sequence) | SEQ. ID No. |
|---|---|---|
| PoP_00026_hsa-let-7f-2 | 5'-GTGCACGAAGCTTCAGCATAGTTATCTCCAAGATGGGGTATGACCCTAAAACTATGCTGAAACTTCGTACACCTTAACCGAACTGACGGCCATCAAGGCTATAGTGAGTCGTATTAGCGCGGGAGCTCTG-3' | 50 |
| PoP_00027_hsa-let-7g | 5'-GTGCACGAAGCTTCAGCACAGTTATCTCCTGTACCGGGTGGTATCATAGACCCTCAAACTGTGCTGAAACTTCGTACACCGGGTACATGCGCCTTACTCCTTGTGCTATAGTGAGTCGTATTAGCGCGGG-3' | 51 |
| PoP-00028_hsa-let 7i | 5'-GTGCACGAAGCTTCAGCGCAGTTATCTCCACAGCGGGCAATGTCACAACCCGACCAACAGCGCTGAAACTTCGTACACCTTCTATTCTAAGCCGGCGGTCATATCTATAGTGAGTCGTATTAGCGCGGTG-3' | 52 |
| PoP_00029_consensus | 5'-GTGCACGAAGCTTCAGCGGGCTCCTTGCCCGCTGAAACTTCGTACACCGCTTGATGCTTTACAAGATCGCGTTCTATAGTGAGTCGTATTAGCGCGGGCAGTGGGTTCTCTAGTTAGCCAGAGAGCTCTG-3' | 53 |

2. PCR Amplification of Template dsDNA.

Template dsDNA was obtained by PCR amplification using Template ssDNA (as to the sequence, see Table 1, synthesized by outsourcer, Greiner) for a RNA probe (PoP_00001_Kt) as a template.

As PCR primers, Forward primer and Reverse primer were used. The composition of a reaction solution (50 μL) was as follows: 1×KOD-Plus-Neo buffer (TOYOBO), 0.2 mM dNTPs, 1.5 mM MgSO4, 0.5 μM DNA primers, 2 Template ssDNA and 0.02 U/μL, KOD-Plus-Neo polymerase (TOYOBO). The reaction was performed by repeating a cycle consisting of a first incubation at 94° C. for 2 minutes, an incubation at 98° C. for 10 seconds and an incubation at 68° C. for 20 seconds, 15 times. The generated PCR product was purified by PCR Purification Kit (QIAGEN). Note that, at the time of elution, ultrapure water (15 μL) was used. Other RNA probes were subjected to the same operation. If a plurality of types of RNA probes were synthesized, PCR was performed by mixing them such that a final concentration of a mixture of all Template ssDNAs reached 2 nM.

3. In-Vitro Transcription from Template dsDNA

A transcription reaction from Template dsDNA was performed by using an in-vitro transcription system (MEGAshortscript™ T7 Transcription Kit, Life Technologies). The composition of a reaction solution (10 μL) was as follows: 1×T7 Reaction Buffer (Life Technologies), 7.5 mM GTP Solution, 7.5 mM ATP Solution, 7.5 mM CTP Solution, 7.5 mM UTP Solution, 150 nM Template dsDNA and 1×T7 Enzyme Mix (Life Technologies). Incubation was carried out at 37° C. for 4 hours. Thereafter, to the reaction solution, 1 μL of TURBO DNase (Life Technologies) was added. The resultant solution was mixed and incubated at 37° C. for 30 minutes. The generated transcriptional product was purified by use of RNeasy MinElute Cleanup Kit (QIAGEN) by modifying Kit protocol. To the transcriptional product, ultrapure water was added to control the volume to be 100 μL. To this, Buffer RLT (350 μL) (QIAGEN) was added and mixed, and subsequently ethanol (700 μL) was added and mixed. The mixture (575 μL) was applied to RNeasy MinElute Spin Column (QIAGEN) set in a 2 mL collection tube (QIAGEN), and centrifuged at 10,000×g, for 15 seconds, and the filtrate was discarded. The remaining mixture was applied to the Column in the same manner and repeatedly centrifuged. Subsequently, to the Spin Column, Buffer RPE (QIAGEN) (500 μL) was added. The mixture was centrifuged at 10,000×g for 15 seconds and the filtrate was discarded. To the Spin Column, 80% ethanol (500 μL) was added. The mixture was centrifuged at 20,400×g for 2 minutes and the filtrate was discarded. The Spin Column was set in a new collection tube and the Column with the lid opened was subjected to centrifugation at 20,400×g, for 5 minutes. The Spin Column was set in a 1.5 mL tube. After ultrapure water (20 μL) was added, centrifugation was performed at 20,400×g for one minute. In this manner, a RNA probe was eluted. The RNA concentration was determined by measuring the absorbance at 260 nm by NanoDrop 2000 (Thermo Fisher Scientific).

4. Cy5 Fluorescence Label for RNA Probe

The 3' ends of the RNA probes synthesized by transcription were modified with pCp Cy5 (Jena Bioscience) by adding it with the help of T4 RNA ligase (cloned) 5 U/μL (Life Technologies). The composition of a reaction solution (20 μL) was as follows: 1× T4 RNA Ligase Buffer (Life Technologies), 50 μM pCp-Cy5 (Jena Bioscience), 6 μM RNA probe and 0.5 U/μL T4 RNA Ligase (Life Technologies). Incubation was carried out at 16° C. for 20 hours. The produced Cy5 labeled RNA probe was purified with RNeasy MinElute Cleanup Kit (QIAGEN) in the same manner as mentioned above. Note that at the time of elution of RNA probe, an operation of adding ultrapure water (15 μL) and centrifuging at 20,400×g for one minute was repeated twice. The RNA concentration was determined by measuring the absorbance at 260 nm, whereas the concentration of Cy5 labeled was determined by measuring the absorbance at 650 nm by use of NanoDrop 2000 (Thermo Fisher Scientific). In this operation, about 90% of the RNA probes were labeled with Cy5.

5. Labeling of Proteins L7Ae and U1A with Cy3

L7Ae and U1A were subjected to *Escherichia coli* purification in accordance with the reports previously published (L7Ae: Saito H, Fujita Y, Kashida S, et al. 2011. Nat. Commun. 2: 160., U1A: Kashida S, Inoue T and Saito H. 2012. Nucleic Acids Res. 40: 9369-78).

L7Ae and U1A were subjected to a Cy3 labeling reaction using Cy3 Mono-Reactive Dye, protein array grade (GE Healthcare). First, a 1.0 mg/mL protein solution (0.20 mL) was added to a dialysis cup of Oscillatory Microdialysis System (8K MWCO) (COSMO Bio Ltd.) and exchange with 0.1 M Sodium-Carbonate Sodium-Bicarbonate (SCSB) buffer (pH 9.3) was performed. To a tube for Cy3 Mono-Reactive Dye (GE Healthcare), dimethyl sulfoxide (30 μL) was added and dissolved. Immediately upon preparation, the dye solution (6 μL) was added to a protein solution and incubated in the dark at room temperature for 30 minutes. During incubation, the reaction solution was stirred by shaking up and down at intervals of 10 minutes. During the reaction time, to Amicon Ultra-0.5 mL Centrifugal Filters (Millipore) set in collection tubes (Millipore), 0.5 mL of TBST buffer (Tris-HCl 20 mM, NaCl 300 mM, 0.1% Tween-20) was added and centrifugation was performed at 4° C. at 14,000×g for 15 minutes. The filtrate was discarded and the filter was equilibrated. The protein solution after the reaction was added to the filter equilibrated. Subsequently, TBST was added up to 0.4 mL and mixed by micropipetting. Thereafter, centrifugation was performed at 4° C. and 14,000×g for 15 minutes and the filtrate was discarded. This operation was repeated three times. This filter was set in a new collection tube upside down and centrifugation was performed at 4° C. and 1,000×g for 2 minutes to collect the protein solution. To the protein solution collected, an equivalent amount of glycerol was added. The resultant solution was stored at −30° C. until it was used in later experiments. The concentration of Cy3 labeled was determined based on the absorbance at 552 nm. The protein concentration was determined by use of protein assay (Bio-Rad) in accordance with the Bradford method.

6. Confirmation of Binding of Cy3-L7Ae and Cy5-RNA Probes by Gel Shift Assay

The binding between DNA Barcode (bc25mer_00001) and Cy5-RNA probe (PoP_00001) and further, the binding between the DNA/RNA complex and Cy3-L7Ae were confirmed by EMSA (Electro Mobility Shift Assay) as follows. First, bc25mer_00001 and a PoP_00001_Kt were mixed and annealed. The composition of a reaction solution (11 μL) was as follows: 500 nM bc25mer_00001, 500 nM PoP_00001_Kt and 1× Annealing Buffer (50 mM HEPES-KOH (ph7.8), 100 mM KCl). The reaction was incubated at 98° C. for 2 minutes and at 55° C. for one minute, and then incubated for 30 minutes while decreasing the temperature at a rate of 1° C. per minute. Subsequently, the DNA/RNA complex annealed and L7Ae were mixed and allowed to bind as follows. The composition of the reaction solution (15 μL) consisted of 0, 100, 200, 500 or 1000 nM Cy3-L7Ae, 50 nM DNA/RNA complex and 1× Annealing Buffer. Incubation was carried out on ice for 30 minutes. To the solution, 3.75 μL of a 5×dye solution (0.25% bromophenol blue, 30% glycerol) was added and mixed. The mixture solution (10 μL) was overlaid on a non-denatured 15% polyacrylamide (1/30 bis-acrylamide) gel and electrophoresis was performed at 4° C. and 200 V for 60 minutes. After the electrophoresis, the gel was stained with SYBR Green I and II at room temperature for 15 minutes, and scanned by Typhoon FLA 7000 (GE Healthcare) in SYBR Green mode (600 pmt) and Cy5 mode (900 pmt). Bands were confirmed. The results are shown in FIGS. 4A-4B. As a result, it was shown that DNA Barcode and a Cy5-RNA probe form a DNA/RNA complex and further that a complex and L7Ae are bound.

7. Design of Custom Array on Which 25-mer DNA Barcode was Spotted

On CGH custom array 8×15K (Agilent), spots of 25-mer DNA Barcode were arranged to design a DNA Barcode microarray. The spots of bc25mer_00001 to bc25mer_00500 DNA Barcodes (to be bound), i.e., bc25mer_1 bc25mer_500, were arranged at a rate of 10 for each and the spots of bc25mer_501 to bc25mer_10667 were arranged at a rate of one for each.

8. RNP Microarray of 12 Types of RNA Probes and L7Ae

Whether or not the RNP interaction between Cy5-RNA probes (PoP_00001 and PoP_000018-28) and Cy3-L7Ae on the DNA Barcode microarray can be detected was tested. To a 1.5 mL tube, 120 ng of Cy5-RNA probe PoP_00001_Kt, 120 ng of Cy5-RNA probe PoP_00018-28 and ultrapure water were mixed and controlled to have a volume of 18 μL. To this, 4.5 μL of 10× Gene Expression Blocking Agent (Agilent) and 22.5 μL of 2× Hi-RPM Hybridization Buffer (Agilent) were added and mixed. The mixture solution was incubated at 100° C. for 5 minutes and subsequently on ice for 5 minutes. On the lower frame of a hybridization chamber (Agilent), a gasket slide (Agilent) was mounted. In a single well of the gasket slide, the mixture solution (45 μL) was added and the well was, covered with a DNA Barcode microarray slide and then a hybridization chamber was assembled. The hybridization chamber was set at a rotor (Agilent) of a hybridization oven of 55° C. Incubation was performed for 20 hours at a rotation rate of 20 per minute. The hybridization chamber was taken out from the oven and made into pieces. The microarray slide was taken out, separated from the gasket in Gene Expression Wash Buffer 1 (Agilent), washed with Gene Expression Wash Buffer 1 at room temperature for 5 minutes and further washed with Gene Expression Wash Buffer 2 (Agilent) at 37° C. for 5 minutes. The dried microarray slide was scanned by a microarray scanner (Agilent) in the mode of 8×15K, c scan, AglilentHD_miRNA, two color, XDR, Hi and Lo (0.05). In this manner, binding of an RNA probe to a target spot was confirmed based on Cy5 signal.

Figure 5:
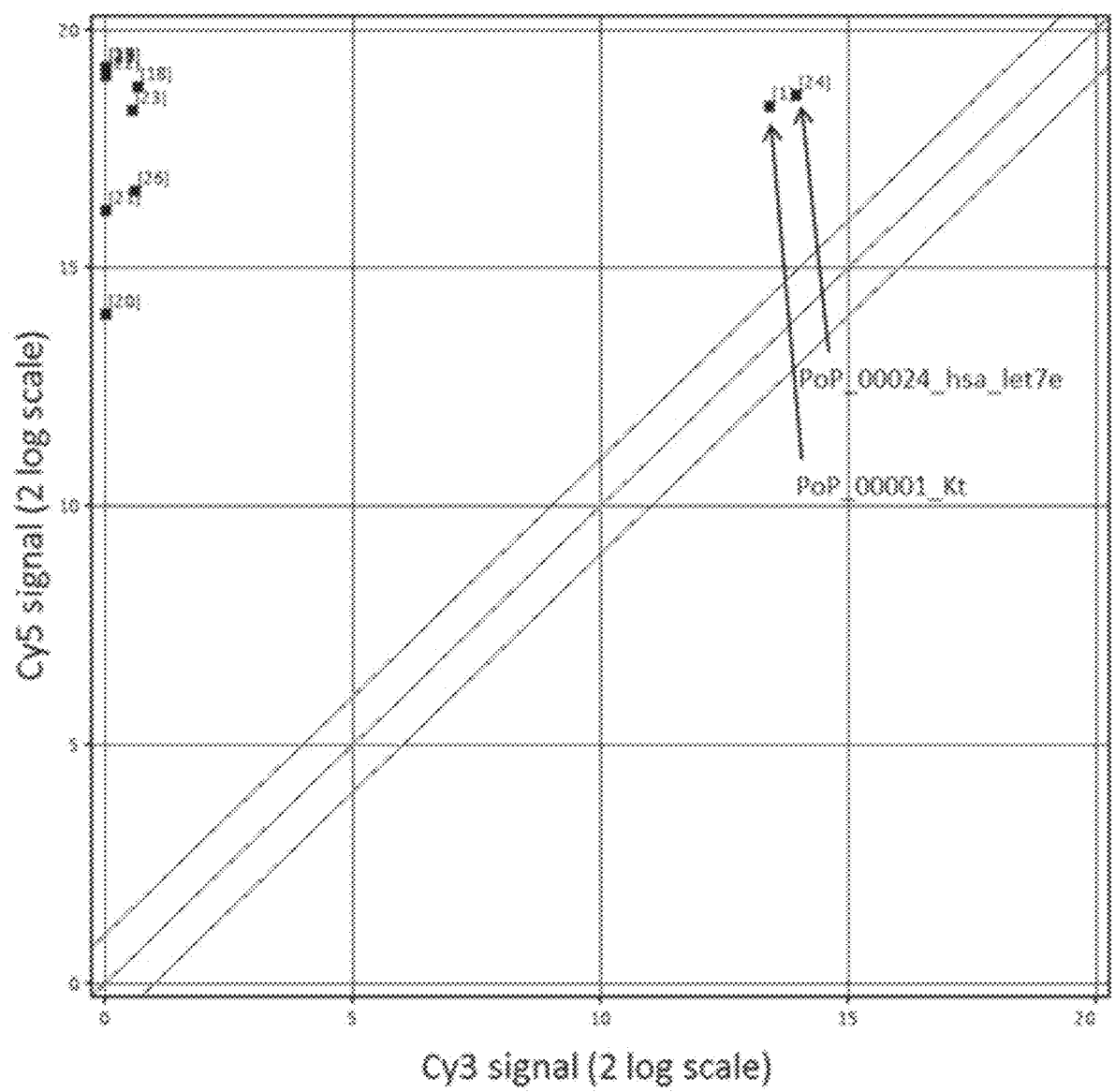
FIG. 5 shows the results of the interactions of PoP_00001 and PoP_000018-28 with. Cy3-L7Ae detected by the RNA microarray.

Subsequently, to the gasket slide on the hybridization chamber, 70 μL of 5 nM Cy3-L7Ae (controlled in concentration with TBSMT buffer (Tris-HCl 20 mM, NaCl 300 mM, 5 mM MgCl$_2$, 0.1% Tween-20)) was added and then a microarray slide scanned was mounted. A hybridization chamber was assembled and incubation was performed at room temperature for 30 minutes. The hybridization chamber was made into pieces and the microarray slide was taken out, separated from the gasket in the TBSMT buffer, washed with TBSMT buffer at room temperature for 5 minutes, and further washed with TBSM buffer (Tris-HCl 20 mM, NaCl 300 mM, 5 mM MgCl$_2$) at room temperature for 5 minutes. The dried microarray slide was scanned again. As a result, as shown in FIG. 5, Cy3 signal at a spot of PoP_00001_Kt serving as a positive control was detected. In addition, Cy3 signal, which was 1.5 times as strong as that at PoP_00001_Kt, was detected at a spot of PoP_00024_hsa-let-7e. No Cy3 signal was detected at spots of other 10 probes.

9. Confirmation of Binding of L7Ae and PoP_00024 Probe by Gel Shift Assay

Figure 6:
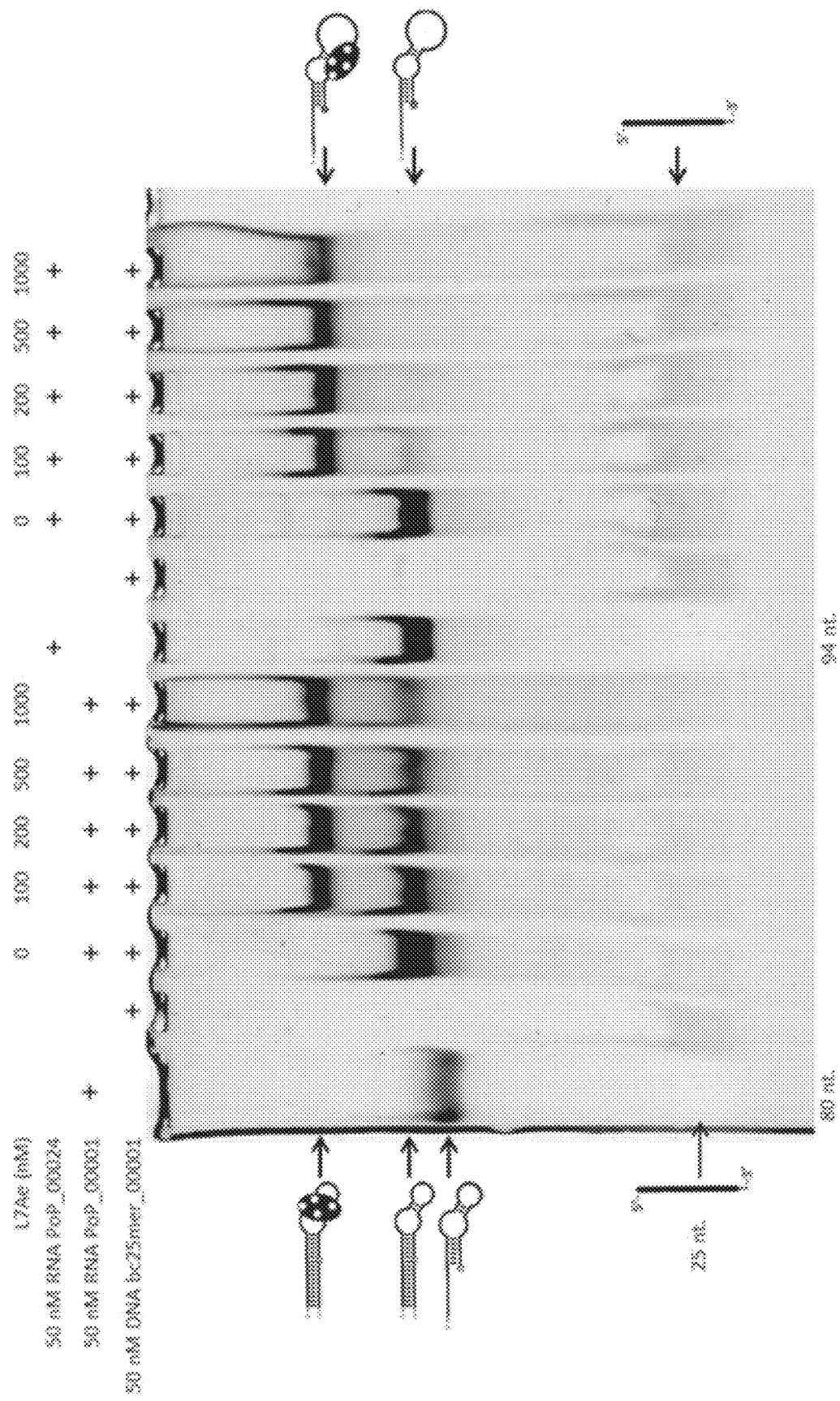
FIG. 6 shows the results of the interaction of PoP_00024 with Cy3-L7Ae checked by gel shift assay.

Specific binding of DNA Barcode (bc25mer_00001) and Cy5-RNA probe (PoP_00001_Kt), and further, binding of Cy5-RNA probe (PoP_00001_Kt, PoP_00024_hsa-let-7e) and L7Ae were confirmed by EMSA as follows. First, bc25mer_00001 and PoP_00001_Kt or PoP_00024_hsa-let-7e were mixed and annealed. The composition of a reaction solution (11 μL) was as follows: 500 nM bc25mer_00001, 500 nM Cy5-RNA probe, 1× Annealing Buffer (50 nM HEPES-KOH (ph7.8), 100 mM KCl). The reaction was incubated at 95° C. for 5 minutes and at room temperature for 10 minutes. Subsequently, the DNA/RNA complex annealed and L7Ae were bound by mixing them as follows. The composition of a reaction solution (15 µL) was as follows: 0, 100, 200, 500 or 1000 nM Cy3-L7Ae, 50 nM DNA/RNA complex and 1× Annealing Buffer. Incubation was performed on ice for one hour. To the solution, 3.75 µL of a 5×dye solution (0.25% bromophenol blue, 30% glycerol) was added and mixed. The mixture solution (10 µL) was overlaid on non-denatured 15% polyacrylamide (1/30 bis-acrylamide) gel and electrophoresis was performed at 4° C. and 200 V for 60 minutes. After the electrophoresis, the gel was stained with SYBR Green I and II at room temperature for 15 minutes, and scanned by Typhoon FLA 7000 (GE Healthcare) in SYBR Green mode (600 pmt). Bands were confirmed. The results are shown m FIG. 6. As a result, it was shown that bc25mer_00001 binds to PoP_00001_Kt to make a complex and does not bind to PoP_00024_hsa-let-7e, and that PoP_00001_Kt and PoP_00024_hsa-let-7e bind to L7Ae; however, PoP_00024_hsa-let-7e binds about 10 times as strong as PoP_00001_Kt. From the foregoing, it was found that the loop, sequence of hsa-let-7e Pre-miRNA binds to L7Ae and the binding affinity is stronger than a known Kt loop. From this, it was suggested that a novel RNA sequence binding to a specific protein can be obtained by the RNP microarray, a technique of the patent application.

10. RNP Microarray of 18 Types of RNA Probes and U1A

Whether the RNP interaction between Cy5-RNA probes (PoP_00001, 00008, 00010, 00011, 00014, 00016 and, PoP_000018-28) and Cy3-U1A on the DNA Barcode microarray can be detected or not was checked.

To a 1.5-mL tube, 120 ng of Cy5-RNA probe PoP_00001_Kt, 120 ng of Cy5-RNA probe PoP_00001, 00008, 00010, 00011, 00014, 00016, PoP_00018-28 and ultrapure water were mixed and controlled to have a volume of 18 µL. Hereinafter, the same operation as described in Section 8 above was performed. Binding of the RNA probe to a target spot was confirmed based on Cy5 signal.

Figure 7:
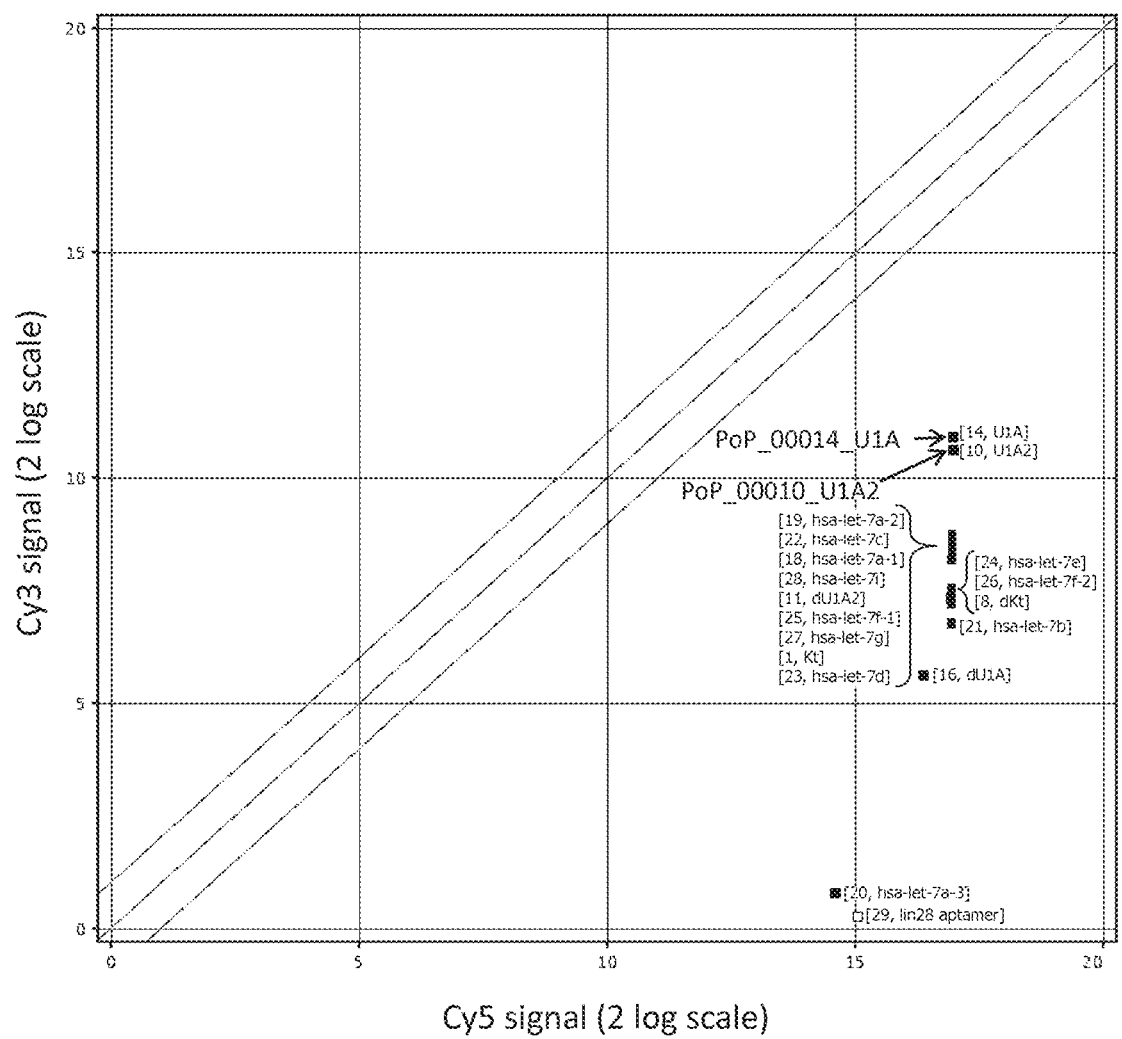
FIG. 7 shows the results of the interactions of 18 types of RNA probes including PoP_00010_U1A2 and PoP_00014_U1A with Cy3-U1A detected by the RNA microarray.

Subsequently, to the gasket slide on the hybridization chamber, 70 µL of 40 nM Cy3 U1A was added and a microarray slide having RNA probes bound thereto was mounted and then a hybridization chamber was assembled. Incubation was performed at room temperature for 30 minutes. The hybridization chamber was made into pieces and the microarray slide was taken out, separated from the gasket in the TBSMT buffer, washed with TBSMT buffer at room temperature for 5 minutes, and further rinsed with TBSM buffer. Thereafter, the dried microarray slide was scanned. As a result, as shown in FIG. 7, Cy3 signal, which was at least 10 times as strong as that of other spots, was detected at spots of PoP_00010_U1A2 and PoP_00014_U1A having U1A binding sequence. From the above, it was suggested that an RNA sequence binding to U1A can be detected by the RNP microarray.

Example 3

In consideration of the results of Example 2, whether or not the interaction between human or mouse Pre-miRNA loop sequence and L7Ae can be detected by the RNP microarray was checked based on Template ssDNA library, which was synthesized in accordance with OLS by an outsourcer and consists of complementary strands of template DNAs of 6500 types of RNA probes (RNP_00001-06500).

1. PCR Amplification of Template dsDNA.

Using the Template ssDNA library, which was synthesized in accordance with OLS by an outsourcer, as a template, Template dsDNA was obtained by PCR amplification in the same operation as in Example 2, Section 2. Note that, the scale of the reaction was 100 µL and elution was performed with ultrapure water (15 µL), twice.

2. In-Vitro Transcription from Template dsDNA

A transcription reaction from Template dsDNA was performed in the same manner as in Example 2, Section 2. Note that, the scale of the reaction was 20 µL, and elution was performed with ultrapure water (15 µL), twice.

3. Cy5 Fluorescence Label for RNA Probe

The 3' ends of RNA probes synthesized by transcription in the same manner as in Example 2, Section 3 were modified with pCp-Cy5. Note that, the scale of the reaction was 100 µL×2.

4. RNP Microarray of 6500 Types of RNA Probes and L7Ae

Whether or not the RNP interaction between Cy5-RNA probes (RNP00001-06500) and Cy3-U1A can be detected on the DNA Barcode microarray was tested.

Figure 8:
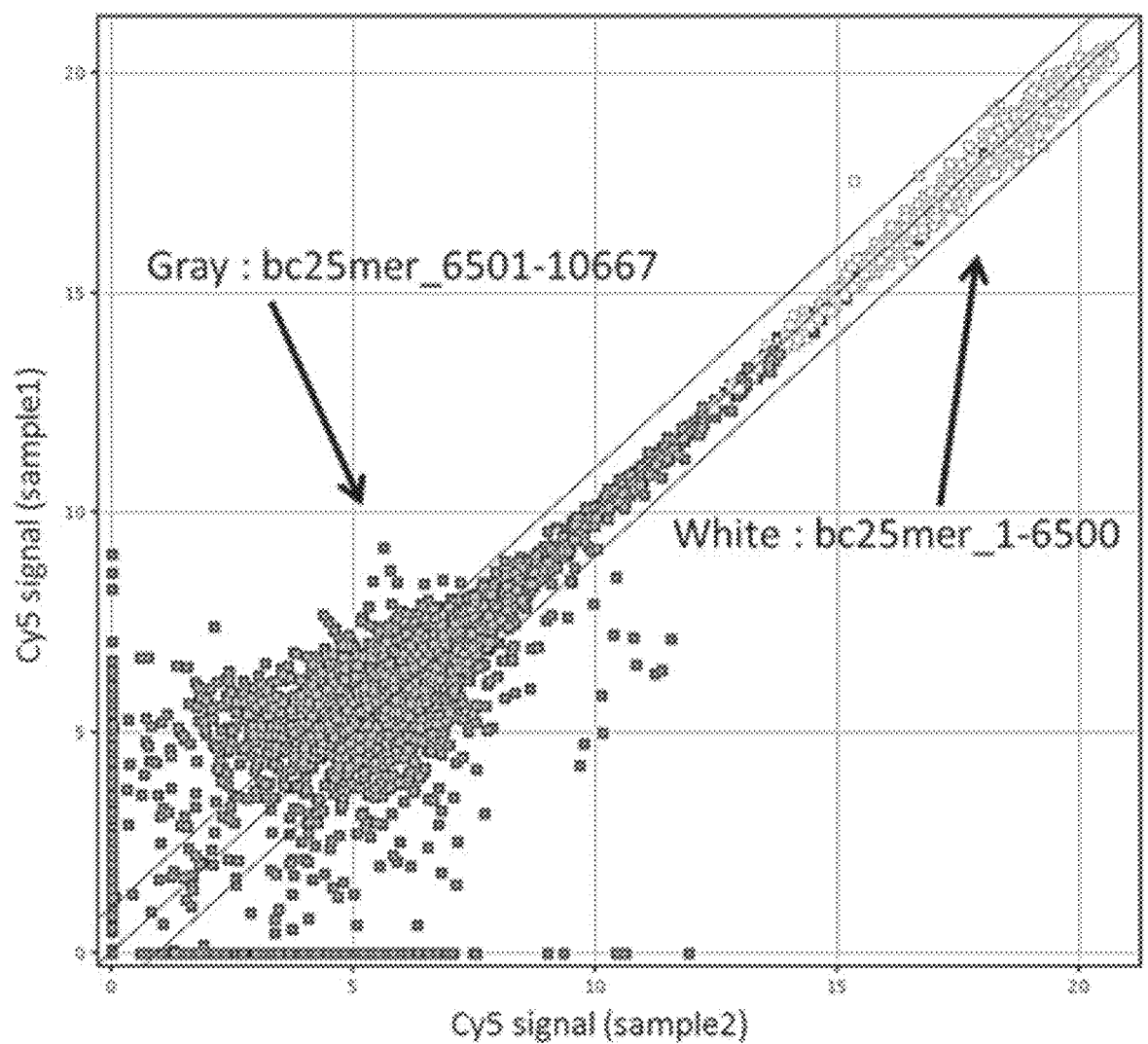
FIG. 8 shows the results of hybridization of RNA probes (RNP_00001-06500) and template DNA.

To a 1.5 mL-tube, 5 µg of Cy5-RNA probe (RNP_00001-06500) and ultrapure water were mixed and controlled to have a volume of 18 µL. Hereinafter, the same operation as described in Example 2, Section 8, was performed. Binding of the RNA probe to a target spot was confirmed based on Cy5. The same operation was performed with respect to a control, i.e., 240 ng of Cy5-RNA probe (PoP_00001, 00008, 00010, 00011, 00014, 00016 and PoP_000018-28). Two samples of each of RNP_00001-06500 and control were subjected to the experiment. As a result, as shown in FIG. 8, Cy5 signal, which was about 15th power to 20th power of 2 as strong as that of RNP_00001-06500, was detected. It was shown that variation in the Cy5 signal intensity between two samples subjecting to the same operation falls within double.

Figure 9:
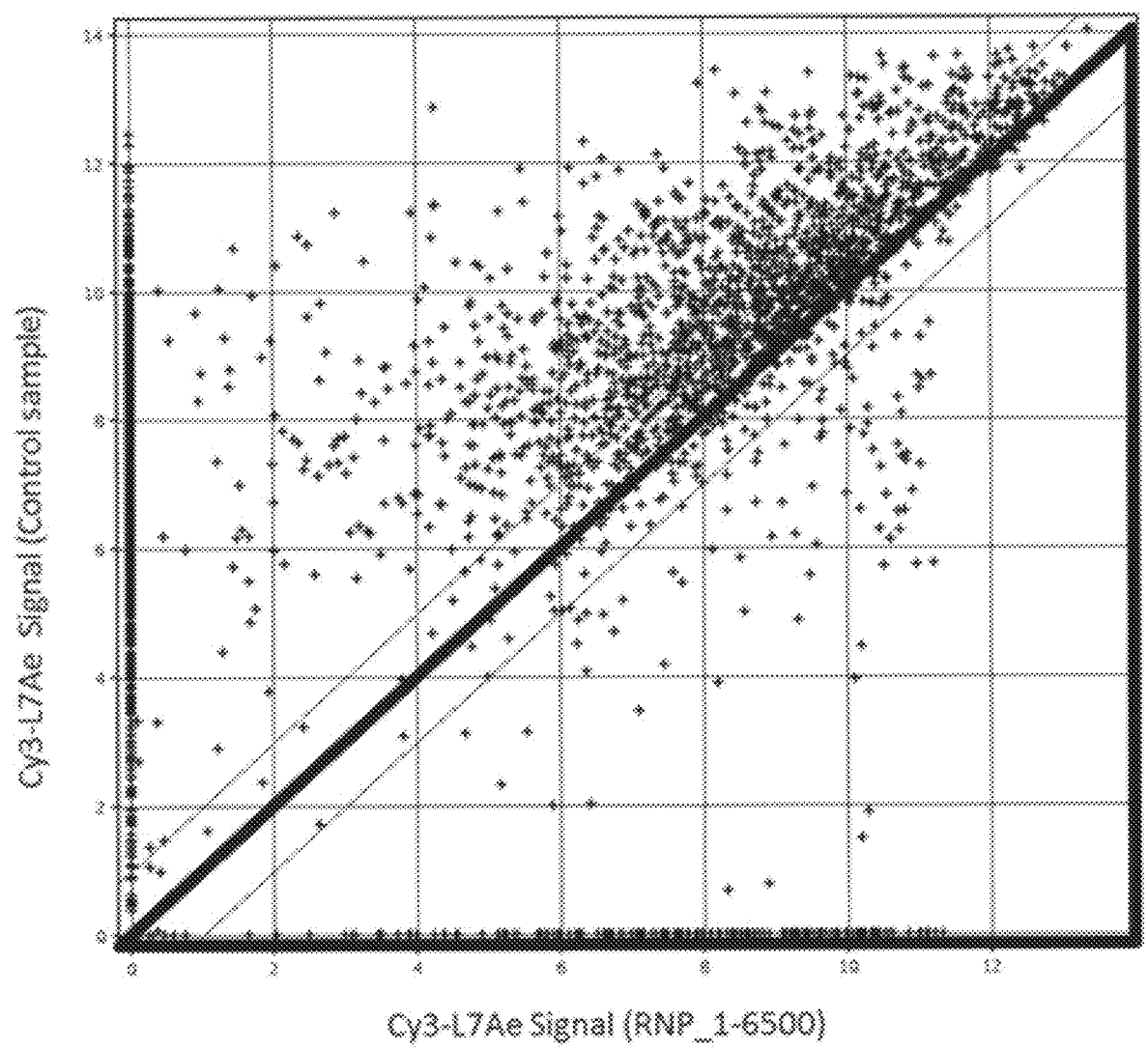
FIG. 9 shows the detection results of RNA probes (RNP_00001-06500) interacting with Cy3-L7Ae by the microarray.

Subsequently, 70 µL of 5 nM Cy3-L7Ae was added to the gasket slide on the hybridization chamber and a microarray slide having RNA probes bound thereto, was mounted. A hybridization chamber was assembled and incubation was performed at room temperature for 30 minutes. The hybridization chamber was made into pieces and the microarray slide was taken out, separated from the gasket in the TBSMT buffer, washed with TBSMT buffer at room temperature for 5 minutes, and further washed with TBSM buffer at room temperature for one minute. Thereafter, the dried microarray slide was scanned. In order to eliminate the signal of Cy3-L7Ae directly bound to the DNA Barcode serving as noise from the resultant data, the following data manipulation was carried out. The Cy3 signal value on the control sample at which RNA probes are not bound and Barcode DNA alone is present (a spot except the spots having 18 types of RNA probes bound thereof) was subtracted from Cy3 signal values of RNP_0001-06500 samples. The spots having the resultant value of 0 or more (within the range of a thick triangular frame in FIG. 9) alone were regarded as a positive (signal) and subjected to analysis. The signal values of two samples were averaged and the resultant signal value of Cy3 was corrected based on the binding amount (Cy5 signal) of RNA probe to the spot in accordance with the following expression: Binding amount (2 log value) of L7Ae=Cy3−Cy5+90

Further, the values of the Cy3 signals of RNA probes having the same loop were averaged and RNA sequences (RNAloop) high in signal were specified by calculation (Table 3). As a result, similarly to Example 2, it was confirmed that RNA sequences containing Kt and hsa-let-7e sequences interact with L7Ae.

TABLE 3

| rank | loop name | loop redundancy | data redundancy | L7Ae-Cy3/Cy5 | cv |
|---|---|---|---|---|---|
| 1 | mmu-mir-466p | 1 | 1 | 13.33902 | 0.006802 |
| 2 | hsa-mir-363 | 2 | 2 | 12.49431 | 0.010773 |
| 3 | mmu-mir-6995 | 1 | 1 | 12.17153 | 0.003218 |
| 4 | hsa-let-7e | 3 | 3 | 12.04553 | 0.005745 |
| 5 | mmu-mir-7061 | 1 | 1 | 11.75058 | 0.016772 |
| 6 | hsa-mir-204 | 3 | 2 | 11.74292 | 0.005552 |
| 7 | mmu-mir-6338 | 1 | 1 | 11.64983 | 0.005225 |
| 8 | hsa-mir-6834 | 3 | 2 | 11.51643 | 0.013116 |
| 9 | hsa-mir-16-2 | 3 | 3 | 11.49918 | 0.007827 |
| 10 | mmu-mir-7220 | 1 | 1 | 11.47272 | 0.001773 |
| 11 | Kt | 1 | 1 | 11.39947 | 0.008828 |
| 12 | hsa-mir-4479 | 3 | 2 | 11.34248 | 0.029844 |
| 13 | hsa-mir-6773 | 3 | 2 | 11.3198 | 0.010137 |
| 14 | hsa-mir-1-2 | 3 | 2 | 11.31454 | 0.006393 |
| 15 | hsa-mir-34a | 3 | 3 | 11.25819 | 0.00778 |

Example 4

Figure 10:
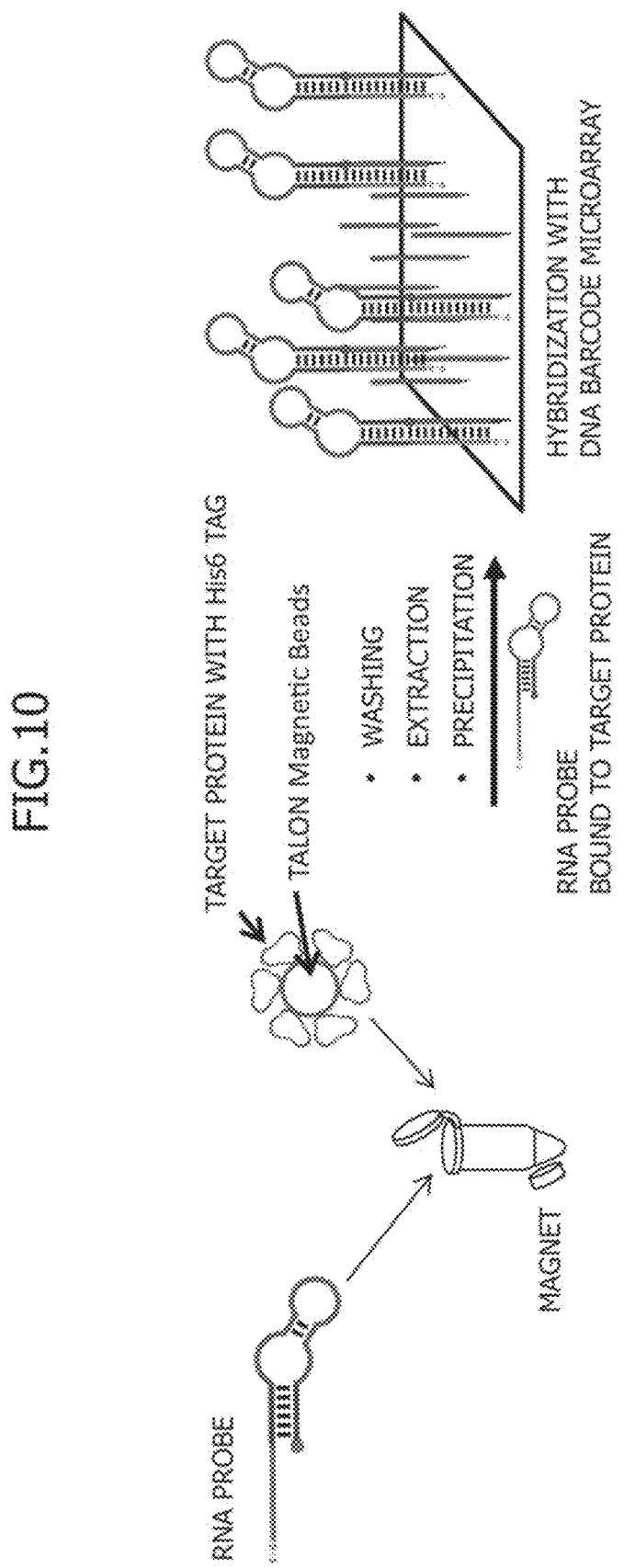
FIG. 10 is a pattern diagram showing, a method for detecting the protein-RNA interaction by a coprecipitation method.
Figure 11:
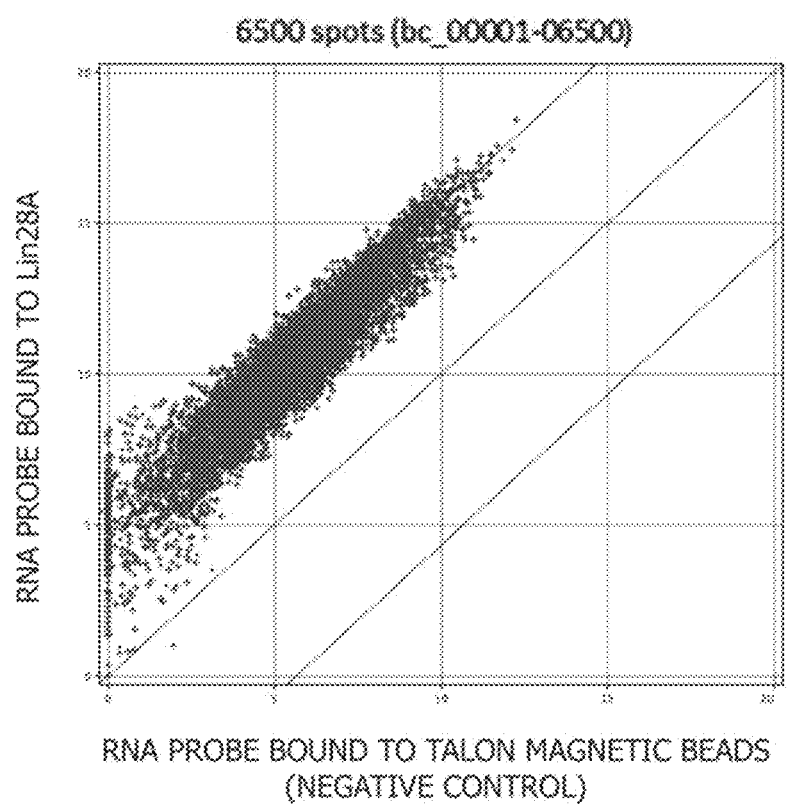
FIG. 11 shows the results of coprecipitation of RNA probes (RNP_00001-06500) interacting with Lin128A, with Lin28A detected, by the microarray. The ordinate shows fluorescence intensity of Cy5 in the case of coprecipitation of RNA probes with Lin28A; whereas the abscissa shows the fluorescence intensity of Cy5 in the case of coprecipitation of RNA probes with beads alone.

Investigation was made on a method for detecting binding to RNA without fluorescence-labeling to a target protein via an ester covalent bond. The method for the ease where Lin28A was used as a target protein will be exemplified (FIG. 10). The method is briefly as follows. Lin28A labeled with a His6 tag (20 pmol), 1 μg of Cy5-RNA probes (RNP_00001-06500) obtained by the method as mentioned above and 20 μL of TALON Magnetic Beads (Clonetech) were dissolved in Protein Binding buffer (20 mM Hepes pH7.8, 80 mM KCl, 20 mM NaCl, 10% glycerol, 2 mM DTT and 0.1 μg/μL BSA) and mixed at 4° C. for 30 minutes. After mixing, TALON Magnetic Beads were magnetically kept within a container and the solution was removed. After the TALON Magnetic Beads were washed with Protein Binding buffer, 200 μL of Elution buffer (1% SDS, 10 mM Tris-HCl and 2 mM EDTA) was added. The mixture was heated at 95° C. for 3 minutes to elute RNA. To the obtained RNA solution, an equivalent amount of phenol was added and the aqueous layer was extracted. Further, an equivalent amount of chloroform was added and the aqueous layer was extracted. To the aqueous layer, 6.6 μL of 3 M NaOAc and 2 μL of Ethachinmate were added and mixed, and further 500 μL of Ethanol was added. Thereafter, the mixture was centrifuged to isolate RNA. The recovered RNA was dissolved in pure water to control the volume to be 18 μL. Hereinafter, the same operation as in Example 2, Section 8, was 1.5 performed for hybridization with DNA Barcode microarray. RNA probes present on the microarray were detected with Cy5 used as index and compared to the results of RNA probes (negative control) detected in the same manner except that Lin28A was not mixed (FIG. 11). Note that, fluorescence intensity of Cy5 (Cy5 Intensity) was calculated as a comparison value to the Cy5 fluorescence intensity (positive control) obtained from Cy5-RNA probe hybridized with DNA Barcode microarray. Of the human RNA probes specifically bound to Lin28A, the top 20 RNA probes exhibiting strong Cy5 Intensity are shown in Table 4. Let-7d, which is known to bind to Lin28A, was detected herein. From this, it was demonstrated that even if a target protein is not fluorescence-labeled, interaction can be detected by pull-down (coprecipitation) with a protein.

Since the number of copies of RNA probes used in this Example is lower than the number of copies of DNA Barcodes spotted on the microarray, the fluorescence intensity increases in proportion to the number of copies of RNA probes bound to Lin28A. Accordingly, it is considered that higher fluorescence intensity means that the RNA probe has higher binding affinity to Lin28A.

TABLE 4

| Rank | loop name | loop redundancy | Cy5 Intensity | SD (Standard deviation) |
|---|---|---|---|---|
| 1 | hsa-let-7d | 3 | 6.812 | 0.205 |
| 2 | hsa-let-7f-1 | 3 | 6.647 | 0.236 |
| 3 | hsa-let-7i | 3 | 6.607 | 0.297 |
| 4 | hsa-mir-1233-1 | 3 | 6.549 | 0.066 |
| 5 | hsa-let-7b | 3 | 6.543 | 0.158 |
| 6 | hsa-mir-4453 | 3 | 6.54 | 0.208 |
| 7 | hsa-mir-598 | 3 | 6.473 | 0.344 |
| 8 | hsa-mir-6775 | 3 | 6.436 | 0.7 |
| 9 | hsa-mir-1233-2 | 3 | 6.433 | 0.033 |
| 10 | hsa-mir-98 | 3 | 6.406 | 0.136 |
| 11 | hsa-mir-6839 | 3 | 6.387 | 0.81 |
| 12 | hsa-mir-5004 | 3 | 6.376 | 0.328 |
| 13 | hsa-mir-6884 | 3 | 6.368 | 0.076 |
| 14 | hsa-mir-6758 | 3 | 6.351 | 0.696 |
| 15 | hsa-let-7g | 3 | 6.332 | 0.01 |
| 16 | hsa-mir-940 | 3 | 6.325 | 0.36 |
| 17 | hsa-mir-4524b | 3 | 6.325 | 0.045 |
| 18 | hsa-mir-4296 | 3 | 6.29 | 0.368 |
| 19 | hsa-mir-4730 | 3 | 6.28 | 0.791 |
| 20 | hsa-mir-638 | 3 | 6.271 | 0.719 |

Example 5

Figure 12:
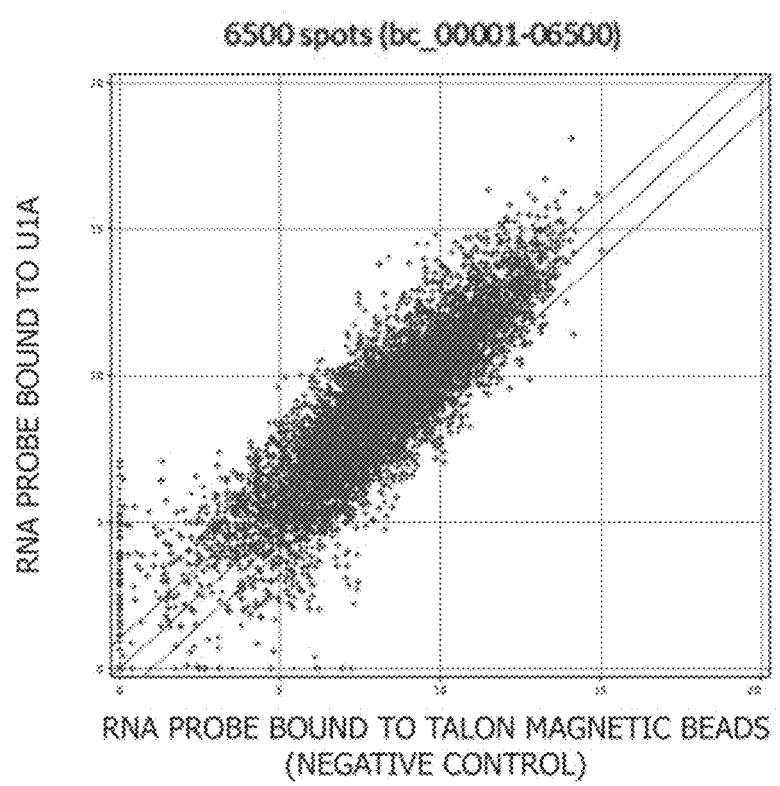
FIG. 12 shows the results of coprecipitation of RNA probes (RNP_00001-06500) interacting with U1A, with U1A detected by the microarray. The ordinate shows fluorescence intensity of Cy5 in the case of coprecipitation of RNA probes with U1A; whereas the abscissa shows the fluorescence intensity of Cy5 in the case of coprecipitation of RNA probes with beads alone.

An RNA probe binding to U1A protein was detected in the same manner as in Example 4. The method is briefly as follows. U1A (20 pmol) labeled with a His6 tag, 1 μg of Cy5-RNA probes (RNP_00001-06500) obtained by the method as mentioned above and 20 μL of TALON Magnetic Beads (Clonetech) were dissolved in Protein Binding buffer (20 mM Hepes pH7.8, 80 mM KCl, 20 mM NaCl, 10% glycerol, 2 nM DTT and 0.1 μg/μL BSA) and mixed at 4° C. for 30 minutes. After mixing, TALON Magnetic Beads were magnetically held in a container and the solution was removed. After the TALON Magnetic Beads were washed with Protein Binding buffer, 200 μL of Elution buffer (1% SDS, 10 mM Tris-HCl and 2 mM EDTA) was added. The mixture was heated at 95'C for 3 minutes to elute RNA. To the obtained RNA solution, an equivalent amount of phenol was added and the aqueous layer was extracted. Further, an equivalent amount of chloroform was added and the aqueous layer was extracted. To the aqueous layer, 6.6 μL of 3 M NaOAc and 2 μL of Ethachinmate were added and mixed, and further 500 μL of Ethanol was added. Thereafter, the mixture was centrifuged to isolate RNA. The recovered RNA was dissolved in pure water to control the volume to be 18 μL. Hereinafter, the same operation as in Example 2, Section 8, was performed for hybridization with DNA Barcode microarray. Note that, in this Example 8×60 K was used as the microarray slide. RNA probes present on the microarray were detected by using Cy5 as index and compared to the results of RNA probe (negative control) which was not mixed with U1A and detected in the same manner (FIG. 12). Note that, the fluorescence intensity of Cy5 (Cy5 Intensity) was calculated as a comparison value to the Cy5 fluorescence intensity (positive control), obtained from Cy5-RNA probe hybridized with DNA Barcode microarray. Of the detected human RNA probes specifically binding, to U1A, the top 20 RNA probes exhibiting strong Cy5 fluorescence intensity (Cy5 Intensity) are shown in Table 5. U1A2, which is known to bind to U1A or U1A, was detected herein. From this, it was demonstrated that an RNA structure, which interacts with a protein except Lin28A, can be detected by the method of the invention.

TABLE 5

| Rank | loop name | loop redundancy | Cy5 Intensity | CV (Coefficient of variation) |
|---|---|---|---|---|
| 1 | U1A2 | 2 | 10.33199055 | 0.351522509 |
| 2 | U1A | 2 | 9.3229175 | 0.499427398 |
| 3 | hsa-mir-6845 | 3 | 9.0601633 | 0.358264439 |
| 4 | hsa-mir-3661 | 3 | 9.0506756 | 0.483975065 |
| 5 | hsa-mir-412 | 2 | 8.94592815 | 4.327160949 |
| 6 | hsa-mir-422a | 2 | 8.783980302 | 5.453123071 |
| 7 | hsa-mir-6796 | 3 | 8.7166514 | 2.003630924 |
| 8 | hsa-mir-7848 | 3 | 8.692771883 | 4.398626947 |
| 9 | hsa-mir-5196 | 3 | 8.671111833 | 4.177130187 |
| 10 | hsa-mir-1302-6 | 3 | 8.554318233 | 1.406353369 |
| 11 | hsa-mir-4723 | 3 | 8.477823733 | 2.762932569 |
| 12 | hsa-mir-493 | 2 | 8.40725935 | 0.421654774 |
| 13 | hsa-mir-637 | 3 | 8.397386267 | 2.906612852 |
| 14 | hsa-mir-378c | 2 | 8.3716097 | 1.132052925 |
| 15 | hsa-mir-4499 | 3 | 8.282939433 | 0.617810759 |
| 16 | hsa-mir-4315-2 | 3 | 8.281862167 | 3.429650103 |
| 17 | hsa-mir-6807 | 3 | 8.277919367 | 2.629366889 |
| 18 | hsa-mir-658 | 3 | 8.2730408 | 1.536251719 |
| 19 | hsa-mir-2682 | 3 | 8.265432467 | 1.61336172 |
| 20 | hsa-mir-1273h | 3 | 8.203573133 | 2.68889337 |

LISTING OF SEQUENCES

PCT_protein and higher-order structure_20150106_142208_10.txt

---

That which is claimed is:

1. A method for detecting RNA which binds to a protein, comprising the following steps:
   (1) a step of bringing a multiplicity of RNA probes into contact with a target protein,
   wherein each RNA probe in the multiplicity of RNA probes comprises:
   (i) a complementary strand sequence to each respective DNA barcode sequence in a multiplicity of DNA barcode sequences;
   (ii) a double stranded stem structure comprising a first stem portion complementary to and hybridized with a second stem portion; and
   (iii) a sequence of a loop portion linking said first and second stem portions,
   wherein each RNA probe is hybridized to each respective complementary DNA barcode sequence in the multiplicity of DNA barcode sequences; and wherein a combination of the sequence (i) and (iii) is different in the multiplicity of RNA probes so that each of the sequence (iii) in the multiplicity of RNA probes sequence can be identified by the corresponding sequence (i), and the sequence (ii) has a common sequence in the multiplicity of RNA probes,
   wherein the multiplicity of DNA barcode sequences is selected from a tag, a zip code, an orthonormal sequence or a barcode sequence so as to prevent cross-hybridization reaction;
   (2) a step of isolating the target protein bound to an RNA probe obtained in step (1) while maintaining binding to the RNA probe,
   (3) a step of extracting the RNA probe from the target protein obtained in step (2),
   (4) a step of bringing the RNA probe obtained in step (3) into contact with a slide having the multiplicity of DNA barcode sequences attached thereto,
   (5) a step of identifying the RNA probe hybridized with the slide, and
   (6) a step of detecting RNA containing the sequence (iii) contained in the RNA probe identified in step (5) as the RNA which binds to the target protein.

2. The method according to claim 1, wherein the sequence of the loop portion is a sequence of a loop portion contained in Pre-miRNA.

3. The method according to claim 1, wherein each RNA probe of the multiplicity of RNA probes has a labeled end.

4. The method according to claim 1, wherein the multiplicity of DNA barcode sequences is spotted to the slide so that each of spots has a different DNA barcode sequence.

5. The method according to claim 4, wherein the RNA probe is identified by a position of the spot on the slide in the identifying step (5).

6. The method according to claim 1, wherein the target protein is bound to a carrier.

7. The method according to claim 6, wherein the carrier is selected from a resin and magnetic beads.

* * * * *

UNITED STATES PATENT AND TRADEMARK OFFICE
CERTIFICATE OF CORRECTION

PATENT NO. : 10,889,853 B2
APPLICATION NO. : 16/562470
DATED : January 12, 2021
INVENTOR(S) : Saito et al.

Page 1 of 1

It is certified that error appears in the above-identified patent and that said Letters Patent is hereby corrected as shown below:

In the Specification

Column 2, Line 38: Please correct "[1] or [3]" to read -- [2] or [3] --

Column 4, Line 2: Please correct "Lin128A" to read -- Lin28A --

Column 26, Line 61: Please correct "Cy3-Cy5+90" to read -- Cy3-Cy5+20 --

Column 28, Line 36: Please correct "2 nM" to read -- 2 mM --

Column 28, Line 42: Please correct "95'" to read -- 95° --

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*